United States Patent
Otsuki et al.

(10) Patent No.: US 11,521,107 B2
(45) Date of Patent: Dec. 6, 2022

(54) LEARNING SYSTEM, REHABILITATION SUPPORT SYSTEM, METHOD, PROGRAM, AND TRAINED MODEL

(71) Applicant: TOYOTA JIDOSHA KABUSHIKI KAISHA, Toyota (JP)

(72) Inventors: Nobuhisa Otsuki, Toyota (JP); Issei Nakashima, Toyota (JP); Manabu Yamamoto, Toyota (JP); Makoto Kobayashi, Nissin (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 329 days.

(21) Appl. No.: 15/931,247

(22) Filed: May 13, 2020

(65) Prior Publication Data
US 2020/0410385 A1    Dec. 31, 2020

(30) Foreign Application Priority Data
Jun. 27, 2019   (JP) .............................. JP2019-120208

(51) Int. Cl.
| | |
|---|---|
| *G16H 20/70* | (2018.01) |
| *G06N 20/00* | (2019.01) |
| *G06N 5/04* | (2006.01) |
| *G16H 50/20* | (2018.01) |
| *G09B 19/00* | (2006.01) |
| *A61H 3/00* | (2006.01) |
| *A61H 1/02* | (2006.01) |

(Continued)

(52) U.S. Cl.
CPC ............. *G06N 20/00* (2019.01); *A61H 1/024* (2013.01); *A61H 3/008* (2013.01); *A63B 22/02* (2013.01); *G06N 5/04* (2013.01); *G09B 19/00* (2013.01); *G16H 20/70* (2018.01); *G16H 50/20* (2018.01); *A61H 2201/501* (2013.01); *A61H 2201/5043* (2013.01); *A61H 2201/5092* (2013.01); *G16H 20/30* (2018.01)

(58) Field of Classification Search
CPC ...................................................... G06F 3/011
See application file for complete search history.

(56) References Cited

U.S. PATENT DOCUMENTS

| | | | |
|---|---|---|---|
| 10,130,311 B1 * | 11/2018 | De Sapio | ............. A61B 5/7455 |
| 2015/0342820 A1 | 12/2015 | Shimada et al. | |

(Continued)

FOREIGN PATENT DOCUMENTS

| | | |
|---|---|---|
| CN | 109933193 A | 6/2019 |
| JP | 6052234 B2 | 12/2016 |

*Primary Examiner* — Di Xiao
(74) *Attorney, Agent, or Firm* — Oliff PLC

(57) ABSTRACT

A learning unit of a learning system generates a learning model, the learning model being configured to input rehabilitation data about rehabilitation and predict feedback control to be performed, the rehabilitation being performed by a trainee using a rehabilitation support system. The rehabilitation support system performs the feedback control based on motivation information of the trainee. The rehabilitation data includes at least training data including the motivation information of the trainee and feedback information indicating the feedback control. The learning unit generates the learning model by using, as teacher data, the rehabilitation data that is obtained when the motivation information is one that causes such a change that the motivation of the trainee is improved.

17 Claims, 13 Drawing Sheets

(51) Int. Cl.
*A63B 22/02* (2006.01)
*G16H 20/30* (2018.01)

(56) References Cited

U.S. PATENT DOCUMENTS

| | | |
|---|---|---|
| 2017/0100637 A1 | 4/2017 | Princen et al. |
| 2017/0173391 A1* | 6/2017 | Wiebe .................... G16Z 99/00 |
| 2020/0135042 A1* | 4/2020 | An ......................... G09B 19/00 |

\* cited by examiner

| DATA SET No. | SETTING PARAMETER | LINE-OF-SIGHT DETECTION DATA | TRAINEE DATA | STAFF DATA | FB INFORMATION: CORRECT-ANSWER LABEL |
|---|---|---|---|---|---|
| 1 | parameter_1 | direction_1 | USER_1 | PT1 | 2 |
| 2 | parameter_2 | direction_2 | USER_2 | PT2 | 1 |
| 3 | parameter_3 | direction_3 | USER_3 | PT3 | 3 |
| 4 | parameter_4 | direction_4 | USER_4 | PT4 | 5 |
| ⋮ | ⋮ | ⋮ | ⋮ | ⋮ | ⋮ |

| | | | <2019.4> | | | |
|---|---|---|---|---|---|---|
| SUN | MON | TUE | WED | THU | FRI | SAT |
| | 1 | 2 | 3 | 4 | 5 | 6 |
| 7 | 8 | 9 | 10 ③→① | 11 ② | 12 | 13 |
| 14 | 15 | 16 | 17 | 18 ⑤ | 19 ⑥ | 20 |
| 21 | 22 | 23 | 24 | 25 | 26 | 27 |
| 28 | 29 | 30 | | | | |

Fig. 10

LEARNING SYSTEM, REHABILITATION SUPPORT SYSTEM, METHOD, PROGRAM, AND TRAINED MODEL

CROSS REFERENCE TO RELATED APPLICATIONS

This application is based upon and claims the benefit of priority from Japanese patent application No. 2019-120208, filed on Jun. 27, 2019, the disclosure of which is incorporated herein in its entirety by reference.

BACKGROUND

The present disclosure relates to a learning system, a rehabilitation support system, a method, a program, and a trained model.

Trainees such as patients may use a rehabilitation support system such as a walking training apparatus when they perform rehabilitation. As an example of the walking training apparatus, Japanese Patent No. 6052234 discloses a walking training apparatus including a walking assistance apparatus that is attached to a leg of a trainee and assists the trainee in walking.

In some rehabilitation support systems, when a trainee performs rehabilitation, a training staff member such as a doctor or a physical therapist may attend the rehabilitation as an assistant for the trainee, give encouraging talks to the trainee, give a helping hand to the trainee, and/or perform a setting operation for the rehabilitation support system.

SUMMARY

Incidentally, in order to obtain good training results, the setting operation of the rehabilitation support system performed by the training staff member needs to be performed so that the rehabilitation support system can appropriately assist the trainee. Further, the timing of the setting operation, i.e., the timing at which assistance is added or ceased, or at which the degree of assistance is changed also affects the training results. Therefore, in order to perform such a setting operation, the training staff member needs to make a choice as to what kind of assistance should be given to the trainee, and determine an appropriate degree of the assistance and its timing. Further, the training staff member needs to determine what kind of encouraging talks he/she should give to the trainee and when he/she should give such talks to the trainee, and determine the timing at which he/she should give a helping hand to the trainee.

It is important that the training staff member should understand a motivation of the trainee in order to make such determinations. This is because keeping the motivation of the trainee (i.e., motivating the trainee to perform training) is important in order to perform rehabilitation based on the motor skill learning theory. For example, the level of difficulty of training that a trainee can accept often changes according to his/her motivation at the time of the training. Therefore, when the trainee performs training regardless of his/her motivation, the result of the training often changes according to the motivation.

However, in the case of the walking training apparatus, since the training staff member often stands behind the trainee, the training staff member cannot directly observe the facial expression of the trainee and hence cannot infer his/her motivation. Further, even in a rehabilitation support system other than the walking training apparatus, the training staff member may not be able to infer the motivation of the trainee. Therefore, the training staff member may not be able to give rehabilitation support while taking the motivation of the trainee into consideration in the rehabilitation support system. Further, the assistance to the trainee is not limited to those given by the training staff member. That is, it is conceivable that the assistance may be given by other kinds of training assistants such as artificial assistants. Even in such cases, a similar problem may arise.

The present disclosure has been made in order to solve the above-described problem and provides a learning system and the like capable of generating a learning model described below. This learning model is a model that predicts feedback control that enables, when a trainee performs rehabilitation using a rehabilitation support system, a training assistant who assists the trainee to give rehabilitation support while taking a motivation of the trainee into consideration.

A first exemplary aspect is a learning system including a learning unit configured to generate a learning model, the learning model being configured to input rehabilitation data about rehabilitation and predict feedback control to be performed, the rehabilitation being performed by a trainee using a rehabilitation support system, the rehabilitation support system being configured to perform the feedback control based on motivation information indicating a motivation of the trainee, in which the rehabilitation data includes at least training data including the motivation information of the trainee and feedback information indicating the feedback control, and the learning unit generates the learning model by using, as teacher data, the rehabilitation data that is obtained when the motivation information is one that causes such a change that the motivation of the trainee is improved. In this way, it is possible to generate a learning model that predicts feedback control that enables, when a trainee performs rehabilitation using the rehabilitation support system, a training assistant who assists the trainee to give rehabilitation support while taking a motivation of the trainee into consideration.

The feedback information may include a setting parameter in the rehabilitation support system when the trainee performs the rehabilitation. In this way, it is possible to construct a learning model so that it can predict, as the feedback control, control related to the setting parameter. The feedback information may include a content of a notification that is provided in the rehabilitation support system when the trainee performs the rehabilitation. In this way, it is possible to construct a learning model so that it can predict, as the feedback control, the content of the notification provided in the rehabilitation support system when the trainee performed the rehabilitation.

The motivation information may include at least information about a line of sight (hereinafter also referred to as line-of-sight information) of the trainee. In this way, it is possible to construct a learning model so that it can predict feedback control in which the line-of-sight information of the trainee is taken into consideration.

The rehabilitation data may include data indicating a preference of the trainee input to the rehabilitation support system. In this way, it is possible to construct a learning model so that it can predict the feedback control in which the preference of the trainee is taken into consideration.

The training data may include data acquired during the rehabilitation by the rehabilitation support system. In this way, it is possible to construct a learning model so that it can predict the feedback control in which the data acquired during the rehabilitation by the rehabilitation support system is taken into consideration.

The rehabilitation data may include trainee data indicating a feature of the trainee. In this way, it is possible to construct a learning model so that it can predict the feedback control in which the feature of the trainee is taken into consideration.

The learning system may further include an extraction unit configured to extract, from rehabilitation data of a plurality of trainees, rehabilitation data of a trainee whose state indicated by index data at an early stage of the training is at a predetermined level, in which the learning unit may generate the learning model for the trainee having the predetermined level by using the rehabilitation data extracted by the extraction unit as an input. In this way, it is possible to construct a learning model so that it can predict feedback control for a trainee whose index data at the early stage of the training is at the predetermined level. The extraction unit may also extract rehabilitation data of a trainee of which a combination of the index data at the early stage of the training and the index data at the time when the index data is at the predetermined level is a predetermined combination. In this way, it is possible to construct a learning model so that it can predict feedback control for a trainee of which the index data at the early stage of the training and the index data at the current stage constitute a predetermined combination.

A second exemplary aspect is a rehabilitation support system capable of accessing a trained model, the trained model being a learning model trained by the learning system according to the first aspect, the rehabilitation support system including: a prediction acquisition unit configured to input the rehabilitation data of a trainee who starts or is performing training to the trained model and obtains a result of a prediction of the feedback control to be performed; and a feedback unit configured to perform the feedback control obtained by the prediction acquisition unit. In this way, when a trainee performs rehabilitation using the rehabilitation support system, a training assistant who assists the trainee can give rehabilitation support while taking a motivation of the trainee into consideration.

A third exemplary aspect is a learning method including a learning step of generating a learning model, the learning model being configured to input rehabilitation data about rehabilitation and predict feedback control to be performed, the rehabilitation being performed by a trainee using a rehabilitation support system, the rehabilitation support system being configured to perform the feedback control based on motivation information indicating a motivation of the trainee, in which the rehabilitation data includes at least training data including the motivation information of the trainee and feedback information indicating the feedback control, and in the learning step, the learning model is generated by using, as teacher data, the rehabilitation data that is obtained when the motivation information is one that causes such a change that the motivation of the trainee is improved. In this way, it is possible to generate a learning model that predicts feedback control that enables, when a trainee performs rehabilitation using the rehabilitation support system, a training assistant who assists the trainee to give rehabilitation support while taking a motivation of the trainee into consideration.

A fourth exemplary aspect is a method for supporting rehabilitation performed in a rehabilitation support system (a method for operating a rehabilitation support system), the rehabilitation support system being capable of accessing a trained model, the trained model being a learning model trained by the learning method according to the third aspect, the method including: an acquisition step of inputting the rehabilitation data of a trainee who starts or is performing training to the trained model and obtaining a result of a prediction of the feedback control to be performed; and a feedback step of performing the feedback control obtained in the acquisition step. In this way, when a trainee performs rehabilitation using the rehabilitation support system, a training assistant who assists the trainee can give rehabilitation support while taking a motivation of the trainee into consideration.

A fifth exemplary aspect is a program for causing a computer to perform a learning step of generating a learning model, the learning model being configured to input rehabilitation data about rehabilitation and predict feedback control to be performed, the rehabilitation being performed by a trainee using a rehabilitation support system, the rehabilitation support system being configured to perform the feedback control based on motivation information indicating a motivation of the trainee, in which the rehabilitation data includes at least training data including the motivation information of the trainee and feedback information indicating the feedback control, and in the learning step, the learning model is generated by using, as teacher data, the rehabilitation data that is obtained when the motivation information is one that causes such a change that the motivation of the trainee is improved. In this way, it is possible to generate a learning model that predicts feedback control that enables, when a trainee performs rehabilitation using the rehabilitation support system, a training assistant who assists the trainee to give rehabilitation support while taking a motivation of the trainee into consideration.

A sixth exemplary aspect is a rehabilitation support program for a computer of a rehabilitation support system, the rehabilitation support system being capable of accessing a trained model, the trained model being a learning model trained by the program according to the fifth aspect, the rehabilitation support program being configured to cause the computer to perform: an acquisition step of inputting the rehabilitation data of a trainee who starts or is performing training to the trained model and obtaining a result of a prediction of the feedback control to be performed; and a feedback step of performing the feedback control obtained in the acquisition step. In this way, when a trainee performs rehabilitation using the rehabilitation support system, a training assistant who assists the trainee can give rehabilitation support while taking a motivation of the trainee into consideration.

A seventh exemplary aspect is a trained model that is any one of learning models trained by the learning system according to the first aspect, the learning method according to the third aspect, and the program according to the fifth aspect. In this way, it is possible to provide a trained model that predicts feedback control that enables, when a trainee performs rehabilitation using a rehabilitation support system, a training assistant who assists the trainee to give rehabilitation support while taking a motivation of the trainee into consideration.

According to the present disclosure, it is possible to provide a learning system that generates a learning model described below. This learning model is a model that predicts feedback control that enables, when a trainee performs rehabilitation using a rehabilitation support system, a training assistant who assists the trainee to give rehabilitation support while taking a motivation of the trainee into consideration. Further, according to the present disclosure, it is possible to provide a rehabilitation support system using the generated trained model, a method and a program for training the learning model, a trained model, and a method and a program for supporting rehabilitation using the trained model.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 6 shows a table for explaining a data set for learning (hereinafter also referred to as learning data set) used in the learning process shown in FIG. 5;

FIG. 10 shows another example of an image presented to a training staff member in the rehabilitation support process shown in FIG. 7;

DESCRIPTION OF EMBODIMENTS

Hereinafter, the present disclosure will be explained through embodiments of the present disclosure. However, they are not intended to limit the scope of the present disclosure according to the claims. Further, all of the components/structures described in the embodiments are not necessarily indispensable as means for solving the problem.

First Embodiment

Figure 1:
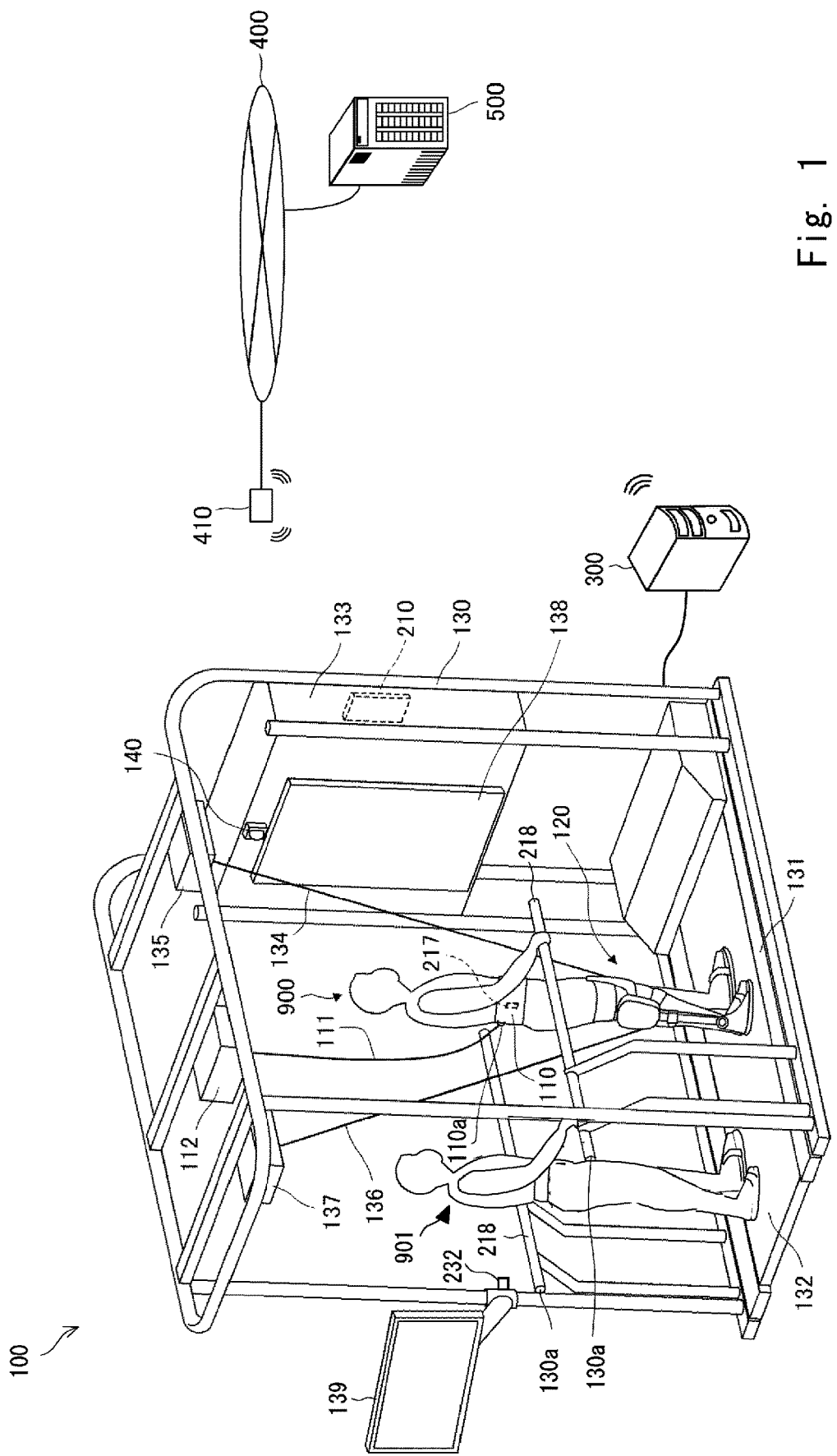
FIG. 1 is a general concept diagram showing an example of a configuration of a rehabilitation support system according to a first embodiment.

A first embodiment will be described hereinafter with reference to the drawings.
(System Configuration)
FIG. 1 is a general concept diagram showing an example of a configuration of a rehabilitation support system according to a first embodiment. The rehabilitation support system (the rehabilitation system) according to this embodiment mainly includes a walking training apparatus 100, an external communication apparatus 300, and a server (a server apparatus) 500.

The walking training apparatus 100 is a specific example of a rehabilitation support apparatus that supports rehabilitation performed by a trainee (a user) 900. The walking training apparatus 100 is an apparatus by which the trainee 900, who is, for example, a hemiplegic patient suffering from paralysis in one of his/her legs, does walking training under the guidance of a training staff member 901. Note that the training staff member 901 can be a therapist (a physical therapist) or a doctor, and may also be referred to as a training instructor, a training assistant, a training supporter, or the like because he/she instructs the trainee in training or assists the trainee by giving assistance and the like. As shown as an example above, the training staff member 901 is a person(s).

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900.

The frame 130 is disposed in a standing position on the treadmill 131 mounted on the floor surface. The treadmill 131 rotates a ring-shaped belt 132 by using a motor (not shown). The treadmill 131 is an apparatus that prompts the trainee 900 to walk, and the trainee 900, who does a walking training, gets on the belt 132 and tries walking in accordance with the movement of the belt 132. Note that the training staff member 901 can stand on the belt 132 behind the trainee 900 and walk together as shown in FIG. 1. However, the training staff member 901 may typically be in a state in which he/she can easily assists the trainee 900 such as standing with his/her feet on both sides of the belt 132.

The frame 130 supports, for example, the control panel 133 that houses an overall control unit 210 that controls motors and sensors, and a training monitor 138 that is formed by, for example, a liquid-crystal panel and shows progress of the training and the like to the trainee 900. Further, the frame 130 supports a front pulling unit 135 roughly above and in front of the head of the trainee 900, supports a harness pulling unit 112 roughly above the head, and supports a rear pulling unit 137 roughly above and behind the head. Further, the frame 130 also includes handrails 130a that the trainee 900 grasps.

The handrails 130a are disposed on the left and right sides of the trainee 900. Each of the handrails 130a is orientated in a direction parallel to the walking direction of the trainee 900. The vertical position and the left/right position of the handrails 130a are adjustable. That is, the handrails 130a may include a mechanism for changing its height and width (i.e., distance therebetween). Further, the handrails 130a can be configured so that their inclination angles can be changed by, for example, adjusting the heights of their front sides and the rear sides in the walking direction to different heights. For example, the handrails 130a can have an inclination angle so that their heights gradually increase along the walking direction.

Further, each of the handrails 130a is equipped with a handrail sensor 218 that detects a load (e.g., a pressure) received from the trainee 900. For example, the handrail sensor 218 may be a resistance change detection-type load detection sheet in which electrodes are arranged in a matrix pattern. Further, the handrail sensor 218 may be a six-axis sensor in which a three-axis acceleration sensor (x, y, z) is combined with a three-axis gyro sensor (roll, pitch, yaw). However, there is no particular limitation on the type of the handrail sensor 218 and the place where the handrail sensor 218 is disposed.

The camera 140 functions as an image pickup unit for observing the whole body of the trainee 900. The camera 140 is disposed near the training monitor 138 and positioned so as to face the trainee. The camera 140 takes still images and/or moving images of the trainee 900 during the training. The camera 140 includes a set of a lens and an image pickup device so that it has such an angle of view that it can shoot the whole body of the trainee 900. The image pickup device is, for example, a CMOS (Complementary Metal-Oxide-Semiconductor) image sensor, and converts an optical image formed on an image forming surface into an image signal.

By the coordinated operation of the front pulling unit 135 and the rear pulling unit 137, the load of the walking assistance apparatus 120 is cancelled so that it does not become a load on the diseased leg. Further, the swinging motion of the diseased leg is assisted according to the set level.

One end of a front wire 134 is connected to a winding mechanism of the front pulling unit 135 and the other end thereof is connected to the walking assistance apparatus 120. The winding mechanism of the front pulling unit 135 winds or pays out the front wire 134 according to the motion of the diseased leg by turning on/off a motor (not shown). Similarly, one end of a rear wire 136 is connected to the winding mechanism of the rear pulling unit 137 and the other end thereof is connected to the walking assistance apparatus 120. The winding mechanism of the rear pulling unit 137 winds or pays out the rear wire 136 according to the motion of the diseased leg by turning on/off a motor (not shown). By the coordinated operation of the front pulling unit 135 and the rear pulling unit 137 as described above, the load of the walking assistance apparatus 120 is cancelled so that it does not become a load on the diseased leg. Further, the swinging motion of the diseased leg is assisted according to the set level.

For example, the training staff member 901, who serves as an operator, increases the set assistance level for a trainee who suffers from severe paralysis. When the assistance level is set to a large value, the front pulling unit 135 winds the front wire 134 with a relatively large force according to the timing of the swinging of the diseased leg. When the training has progressed and the assistance is no longer required, the training staff member 901 sets the assistance level to the minimum value. When the assistance level is set to the minimum value, the front pulling unit 135 winds the front wire 134 according to the timing of the swinging of the diseased leg with a force by which only the weight of the walking assistance apparatus 120 itself is cancelled.

The walking training apparatus 100 includes a fall-prevention harness apparatus as a safety apparatus, which includes, as its main components, a harness 110, a harness wire 111, and a harness pulling unit 112. The harness 110 is a belt that is wound around the abdomen of the trainee 900 and is fixed to his/her waist by, for example, a hook-and-loop fastener. The harness 110 includes a connection hook 110a that connects one end of the harness wire 111, which serves as a hoisting tool, to the harness 110, and may be referred to as a hanger belt. The trainee 900 attaches the harness 110 to his/her diseased leg so that the connection hook 110a is positioned in the rear part of the diseased leg.

One end of the harness wire 111 is connected to the connection hook 110a of the harness 110 and the other end thereof is connected to a winding mechanism of the harness pulling unit 112. The winding mechanism of the harness pulling unit 112 winds or pays out the harness wire 111 by turning on/off a motor (not shown). By the above-described configuration, when the trainee 900 is about to fall down, the fall-prevention harness apparatus winds the harness wire 111 according to an instruction from the overall control unit 210, which has detected the falling-down movement of the trainee 900, and thereby supports the upper body of the trainee 900 by the harness 110, so that the trainee 900 is prevented from falling down.

The harness 110 includes a posture sensor 217 for detecting the posture of trainee 900. The posture sensor 217 is, for example, a combination of a gyro sensor and an acceleration sensor, and outputs an inclination angle of the abdomen, to which the harness 110 is attached, with respect to the direction of gravity.

A management monitor 139 is attached to the frame 130 and serves as a display/input device by which the training staff member 901 or the like monitors and operates the rehabilitation support system. The management monitor 139 is formed by, for example, a liquid crystal panel. Further, a touch panel is disposed over its surface. The management monitor 139 displays various menu items related to the training setting, various parameter values during the training, training results, and so on. Further, an emergency stop button 232 is provided near the management monitor 139. When the training staff member 901 pushes the emergency stop button 232, the walking training apparatus 100 immediately stops its operation.

The walking assistance apparatus 120 is attached to the diseased leg of the trainee 900 and assists the trainee 900 in walking by reducing the load of the extension and flexion at the knee joint of the diseased leg. The walking assistance apparatus 120 includes a sensor or the like that measures the load (e.g., the pressure) on the sole of the foot, and outputs various data related to the moving leg to the overall control unit 210. Further, the harness 110 can be connected to the walking assistance apparatus 120 by using a connection member (hereinafter referred to as a hip joint) including a rotation part. Details of the walking assistance apparatus 120 will be described later.

The overall control unit 210 generates rehabilitation data that may include setting parameters related to the training setting, various data related to the moving leg output from the walking assistance apparatus 120 as a result of training, and so on. The rehabilitation data may include, for example, data indicating the training staff member 901 or indicating his/her years of experience, level of proficiency, etc., data indicating the symptom, the walking ability, the degree of recovery, etc., of the trainee 900, various data output from sensors and the like provided outside the walking assistance apparatus 120. Note that details of the rehabilitation data will be described later.

The external communication apparatus 300 is a specific example of transmission means for transmitting the rehabilitation data to the outside. The external communication apparatus 300 may have a function of receiving and temporarily storing rehabilitation data output from the walking training apparatus 100 and a function of transmitting the stored rehabilitation data to the server 500.

The external communication apparatus 300 is connected to the control panel 133 of the walking training apparatus 100 through, for example, a USB (Universal Serial Bus) cable. Further, the external communication apparatus 300 is connected to a network 400 such as the Internet or an intranet through a wireless communication apparatus 410 by, for example, a wireless LAN (Local Area Network).

Note that the walking training apparatus 100 may be equipped with a communication apparatus instead of using the external communication apparatus 300.

The server 500 is a specific example of the storage means for storing rehabilitation data. The server 500 is connected to the network 400 and has a function of accumulating rehabilitation data received from the external communication apparatus 300. The function of the server 500 will be described later.

In the first embodiment, the walking training apparatus 100 is described as an example of the rehabilitation support apparatus. However, the rehabilitation support apparatus is not limited to this example and may be a walking training apparatus having a different configuration. That is, the rehabilitation support apparatus may be an arbitrary rehabilitation support apparatus that supports rehabilitation performed by a trainee. For example, the rehabilitation support apparatus may be an upper-limb rehabilitation support apparatus that supports rehabilitation of a shoulder(s) or an arm(s). Alternatively, the rehabilitation support apparatus may be a rehabilitation support apparatus that supports rehabilitation for a balancing ability of a trainee.

Figure 2:
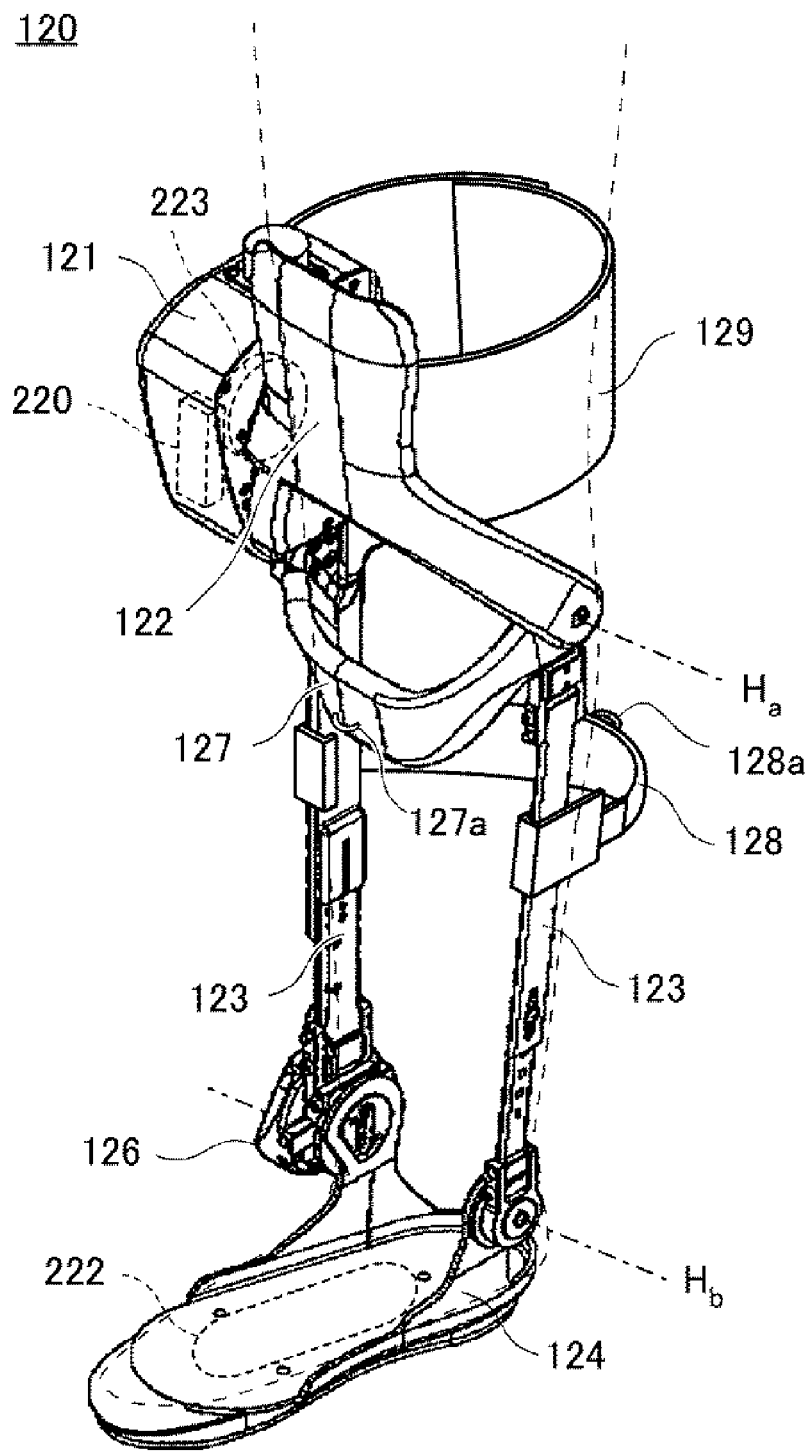
FIG. 2 is a schematic perspective view showing an example of a configuration of a walking assistance apparatus in the rehabilitation support system shown in FIG. 1.

Next, the walking assistance apparatus 120 will be described with reference to FIG. 2. FIG. 2 is a schematic perspective view showing an example of a configuration of the walking assistance apparatus 120. The walking assistance apparatus 120 mainly includes a control unit 121, a plurality of frames that support each part of a diseased leg, and a load sensor 222 for detecting a load (e.g., a pressure) applied to the sole.

The control unit 121 includes an assistance control unit 220 that controls the walking assistance apparatus 120, and also includes a motor(s) (not shown) that generates a driving force(s) for assisting extending movements and flexing movements of the knee joint. The frames, which support each part of the diseased leg, includes an upper-leg frame 122 and a lower-leg frame 123 rotatably connected to the upper-leg frame 122. Further, the frames also include a sole frame 124 rotatably connected to the lower-leg frame 123, a front connection frame 127 for connecting a front wire 134, and a rear connection frame 128 for connecting a rear wire 136.

The upper-leg frame 122 and the lower-leg frame 123 rotate relative to each other around a hinge axis $H_a$ shown in the figure. The motor of the control unit 121 rotates according to an instruction from the assistance control unit 220, and by doing so, force the upper-leg frame 122 and the lower-leg frame 123 to open relative to each other around the hinge axis $H_a$ or force them to close relative to each other. The angle sensor 223 housed in the control unit 121 is, for example, a rotary encoder and detects an angle between the upper-leg frame 122 and the lower-leg frame 123 around the hinge axis $H_a$. The lower-leg frame 123 and the sole frame 124 rotate relative to each other around a hinge axis $H_b$ shown in the figure. The angular range of their relative rotation is adjusted in advance by an adjustment mechanism 126.

The front connection frame 127 is disposed so as to extend in the left/right direction in front of the upper leg and is connected to the upper-leg frame 122 at both ends. Further, a connection hook 127a for connecting the front wire 134 is provided at or near the center of the front connection frame 127 in the left/right direction. The rear connection frame 128 is disposed so as to extend in the left/right direction behind the lower leg and is connected to the lower-leg frame 123 at both ends. Further, a connection hook 128a for connecting the rear wire 136 is provided at or near the center of the rear connection frame 128 in the left/right direction.

The upper-leg frame 122 includes an upper-leg belt 129. The upper-leg belt 129 is a belt integrally provided in the upper-leg frame and is wound around the upper leg of the diseased leg to fix the upper-leg frame 122 to the upper leg. In this way, the whole walking assistance apparatus 120 is prevented from being displaced from the leg of the trainee 900.

The load sensor 222 is a load sensor embedded in the sole frame 124. The load sensor 222 may be configured to detect a magnitude and a distribution of a vertical load (e.g., a vertical pressure) received by the sole of the trainee 900. For example, the load sensor 222 may be configured to detect a COP (Center Of Pressure) of the sole. The load sensor 222 is, for example, a resistance change detection-type load detection sheet in which electrodes are arranged in a matrix pattern.

Figure 3:
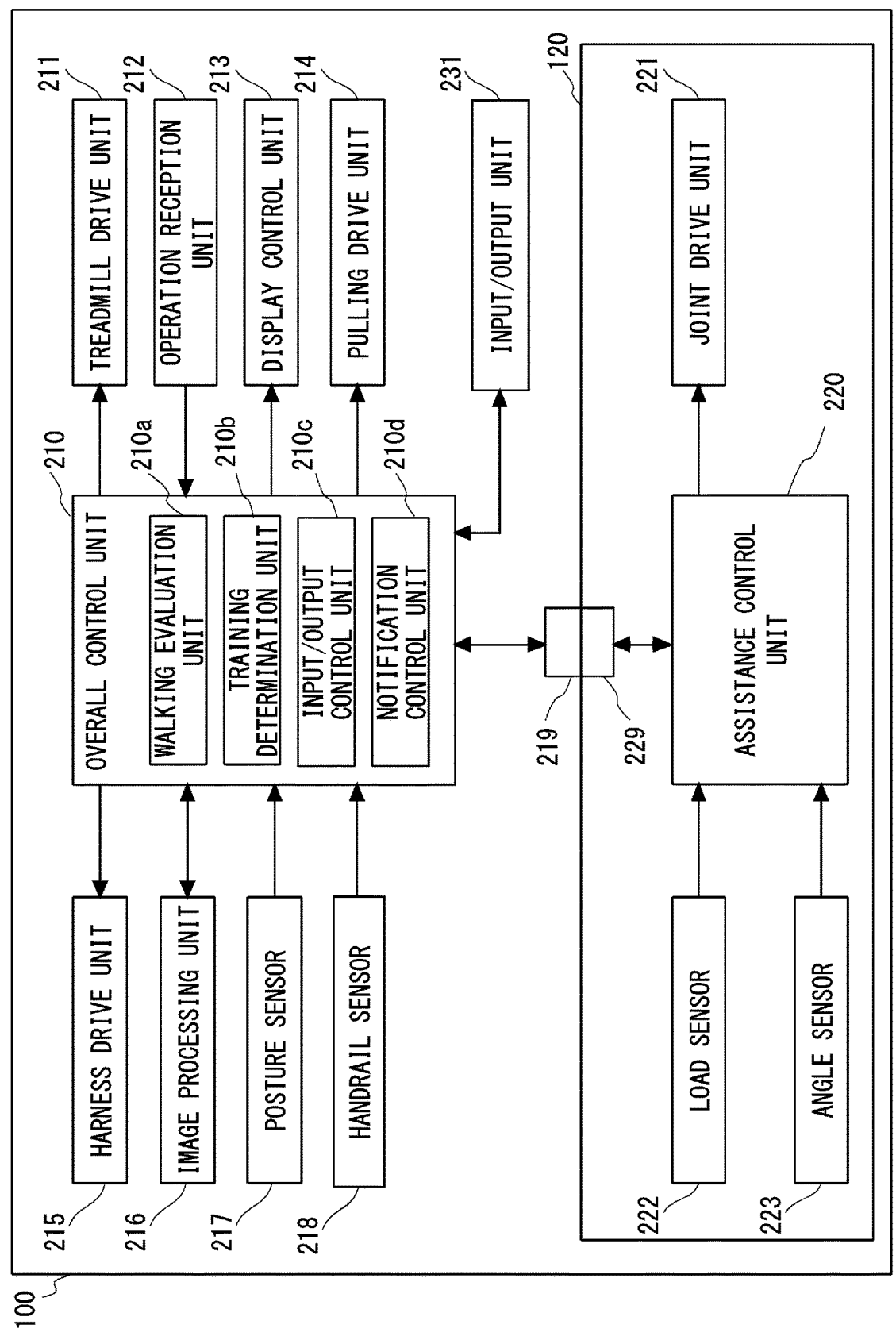
FIG. 3 is a block diagram showing an example of a system configuration of a walking training apparatus in the rehabilitation support system shown in FIG. 1.

Next, an example of a system configuration of the walking training apparatus 100 will be described with reference to FIG. 3. FIG. 3 is a block diagram showing an example of a system configuration of the walking training apparatus 100. As shown in FIG. 3, the walking training apparatus 100 may include an overall control unit 210, a treadmill drive unit 211, an operation reception unit 212, a display control unit 213, and a pulling drive unit 214. Further, the walking training apparatus 100 may include a harness drive unit 215, an image processing unit 216, a posture sensor 217, a handrail sensor 218, a communication connection IF (interface) 219, an input/output unit 231, and a walking assistance apparatus 120.

The overall control unit 210 is, for example, an MPU (Micro Processing Unit) and controls the overall operations of the apparatus by executing a control program loaded from a system memory. The overall control unit 210 may include a walking evaluation unit 210a, a training determination unit 210b, an input/output control unit 210c, and a notification control unit 210d, all of which will be described later.

The treadmill drive unit 211 includes a motor that rotates the belt 132 and its drive circuit. The overall control unit 210 controls the rotation of the belt 132 by sending a drive signal to the treadmill drive unit 211. The overall control unit 210 adjusts, for example, the rotational speed of the belt 132 according to a walking speed set by the training staff member 901.

The operation reception unit 212 receives an input operation from the training staff member 901 and transmits an operation signal to the overall control unit 210. The training staff member 901 operates operation buttons provided in the apparatus, a touch panel disposed over the management monitor 139, an accessory remote controller, etc., which constitute the operation reception unit 212. By the above-described operation, the training staff member can turn on/off the power, provide an instruction to start training, enter a numerical value for the setting, and select a menu item. Note that the operation reception unit 212 can also receive an input operation from the trainee 900.

The display control unit 213 receives a display signal from the overall control unit 210, generates a display image, and displays the generated display image on the training monitor 138 or the management monitor 139. The display control unit 213 generates an image showing progress of the training and a real-time video image shot by the camera 140.

The pulling drive unit 214 includes a motor for pulling the front wire 134 and its drive circuit, which constitute the front pulling unit 135, and a motor for pulling the rear wire 136 and its drive circuit, which constitute the rear pulling unit 137. The overall control unit 210 controls winding of the front wire 134 and winding of the rear wire 136 by sending a drive signal(s) to the pulling drive unit 214. Further, the pulling force of each wire is controlled by controlling the driving torque of the respective motor in addition to controlling the winding operation. The overall control unit 210 identifies (i.e., determines), for example, a timing at which the diseased leg changes from a stance state to a swing state from the result of the detection by the load sensor 222, and assists the swinging action of the diseased leg by increasing or decreasing the pulling force of each wire in synchronization with the identified timing.

The harness drive unit 215 includes a motor for pulling the harness wire 111 and its drive circuit, which constitute the harness pulling unit 112. The overall control unit 210 controls winding of the harness wire 111 and the pulling force of the harness wire 111 by sending a drive signal(s) to the harness drive unit 215. For example, when the overall control unit 210 predicts that the trainee 900 will fall down, it prevents the trainee from falling down by winding the harness wire 111 by a certain length.

The image processing unit 216 is connected to the camera 140, so that it can receive an image signal from the camera 140. The image processing unit 216 receives an image signal from the camera 140 according to an instruction from the overall control unit 210, and generates image data by performing image processing on the received image signal. Further, the image processing unit 216 can also perform a specific image analysis by performing image processing on the image signal received from the camera 140 according to an instruction from the overall control unit 210. For example, the image processing unit 216 detects the position of the foot of the diseased leg at which the foot is in contact with the treadmill 131 (i.e., a stance position) by the image analysis. Specifically, for example, the image processing unit 216 extracts an image area near the tip of the sole frame 124, and calculates the stance position by analyzing an identification marker drawn on a part of the belt 132 where the tip of the sole frame 124 is located.

The posture sensor 217 detects an inclination angle of the abdomen of the trainee 900 with respect to the direction of gravity as described above, and transmits a detection signal to the overall control unit 210. The overall control unit 210 calculates the posture of the trainee 900, in particular, an inclination angle of his/her trunk by using the detection signal from the posture sensor 217. Note that the overall control unit 210 and the posture sensor 217 may be connected to each other through a cable or through short-range wireless communication.

The handrail sensor 218 detects a load (e.g., a pressure) applied to the handrail 130a. That is, the amount of the load corresponding to the part of the trainee's own weight that the trainee 900 cannot support by both legs is applied to the handrails 130a. The handrail sensor 218 detects this load and transmits a detection signal to the overall control unit 210.

The overall control unit 210 also serves as a function execution unit that performs various arithmetic operations and controls related to the overall control. The walking evaluation unit 210a evaluates whether the walking motion of the trainee 900 is abnormal or not by using data acquired from various sensors. The training determination unit 210b determines a training result of a series of walking trainings based on, for example, a cumulative number of the abnormal walking evaluated by the walking evaluation unit 210a. The overall control unit 210 can generate, as part of the rehabilitation data, a result of this determination or the cumulative number of the abnormal walking, based on which the determination result has been obtained.

Note that the determination method, including its criterion, is not limited to any particular methods. For example, the determination can be made by comparing an amount of movement of the paralyzed body part with a reverence value in each walking phase. Note that the walking phases are defined, for example, by classifying (i.e., dividing) one walking cycle of the diseased leg (or a normal leg) into a stance phase in a stance state, a transition phase from the stance phase to a swing phase in a swing state, the swing phase, a transition phase from the swing phase to the stance phase, etc. The walking phase can be classified (determined) based on, for example, the detection result of the load sensor 222 as described above. Note that although the walking cycle can be regarded as one cycle including a stance phase, a transitional phase, a swing phase, and another transitional phase as described above, any of these phases can be defined as the start phase. Alternatively, the walking cycle can be regarded as one cycle including, for example, a double-leg support state, a single-leg (diseased-leg) support state, a double-leg support state, and a single-leg (normal-leg) support state. Even in this case, any state may be defined as the start state.

Further, the walking cycle in which attention is paid to the right leg or the left leg (the normal leg or the diseased leg) can be further subdivided. For example, the stance phase can be divided into an initial ground contact and other four sub-phases, and the swing phase can be divided into three sub-phases. The initial ground contact means a moment when the observed foot touches the floor, and the four sub-phases of the stance phase means a load response phase, a mid-stance phase, a terminal stance phase, and a pre-swing phase. The load response phase is a period from the initial ground contact to when the opposite foot comes off the floor (opposite-foot-off). The mid-stance is a period from the opposite-foot-off to when the heel of the observed foot comes off the floor (heel-off). The terminal stance phase is a period from the heel-off to an initial ground contact on the opposite side. The pre-swing phase is a period from the initial ground contact on the opposite side to when the observed foot comes off the floor (foot-off). The three sub-phases of the swing phase mean an initial swing phase, a mid-swing phase, and a terminal swing phase. The initial swing phase is a period from the end of the pre-swing phase (the aforementioned foot-off) to when both feet cross each other (foot crossing). The mid-swing phase is a period from the foot crossing to when the tibia becomes vertical (vertical tibia). The terminal swing phase is a period from the vertical tibia to the next initial ground contact.

The communication connection IF 219 is an interface connected to the overall control unit 210, and is an interface for providing an instruction to the walking assistance apparatus 120 attached to the diseased leg of the trainee 900 and receiving sensor information therefrom.

The walking assistance apparatus 120 may include a communication connection IF 229 that is connected to the communication connection IF 219 through a cable or wirelessly. The communication connection IF 229 is connected to the assistance control unit 220 of the walking assistance apparatus 120. The communication connection IFs 219 and 229 are communication interfaces in conformity with communication standards, such as those of a wired LAN or a wireless LAN.

Further, the walking assistance apparatus 120 may include an assistance control unit 220, a joint drive unit 221, a load sensor 222, and an angle sensor 223. The assistance control unit 220 is, for example, an MPU and controls the walking assistance apparatus 120 by executing a control program according to an instruction from the overall control unit 210. Further, the assistance control unit 220 notifies the overall control unit 210 of the state of the walking assistance apparatus 120 through the communication connection IFs 229 and 219. Further, the assistance control unit 220 performs control of walking assistance apparatus 120, such as the start/stop thereof, in response to a command from the overall control unit 210.

The joint drive unit 221 includes a motor of the control unit 121 and its drive circuit. The assistance control unit 220 sends a drive signal to the joint drive unit 221 to force the upper-leg frame 122 and the lower-leg frame 123 to open relative to each other around the hinge axis $H_a$ or force them to close relative to each other. Through the above-described operations, the assistance control unit 220 assists an extending motion and a flexing motion of the knee and prevents the knee from buckling.

The load sensor 222 detects the magnitude and the distribution of the vertical load (e.g., the vertical pressure) applied to the sole of the trainee 900 and transmits a detection signal to the assistance control unit 220 as described above. The assistance control unit 220 receives and analyzes the detection signal, and thereby determines the swing/stance state and estimates the switching therebetween.

The angle sensor 223 detects the angle between the upper-leg frame 122 and the lower-leg frame 123 around the hinge axis $H_a$ and transmits a detection signal to the assistance control unit 220 as described above. The assistance control unit 220 receives this detection signal and calculates the open angle of the knee joint.

The input/output unit 231 includes, for example, a USB (Universal Serial Bus) interface and is a communication interface for connecting to an external apparatus (an external communication apparatus 300 or other external apparatus). The input/output control unit 210c of the overall control unit 210 communicates with the external apparatus through the input/output unit 231, rewrites the above-described control program stored in the overall control unit 210 and the control program stored in the assistance control unit 220, receives commands, outputs generated rehabilitation data, and so on. The walking training apparatus 100 communicates with the server 500 through the input/output unit 231 and the external communication apparatus 300 under the control of the input/output controller 210c. For example, the input/output control unit 210c can control the transmission of rehabilitation data to the server 500 and the reception of a command from the server 500 through the input/output unit 231 and the external communication apparatus 300.

When it is necessary to provide a notification to the training staff member 901, the notification control unit 210d provides the notification from the management monitor 139 or a separately-provided speaker(s) by controlling the display control unit 213 or a separately-provided sound control unit or the like. The situation in which it is necessary to provide a notification to the training staff member 901 may include a situation in which a command for providing a notification is received from the server 500. Details of this notification will be described later.

Next, the server 500 will be described in detail. As described above, the walking training apparatus 100 transmits various rehabilitation data to the server 500 through the external communication apparatus 300. The server 500 may be configured so as to receive rehabilitation data from a plurality of walking training apparatuses 100. In this way, the server 500 can collect a number of rehabilitation data. Further, the server 500 is a processing apparatus that processes various data. For example, the server 500 can function as a learning apparatus (a learning system) that constructs a trained model by performing machine learning by using collected rehabilitation data. The learning apparatus can also be a learning machine. Note that the learning apparatus may also be referred to as a learning model generation apparatus.

Figure 4:
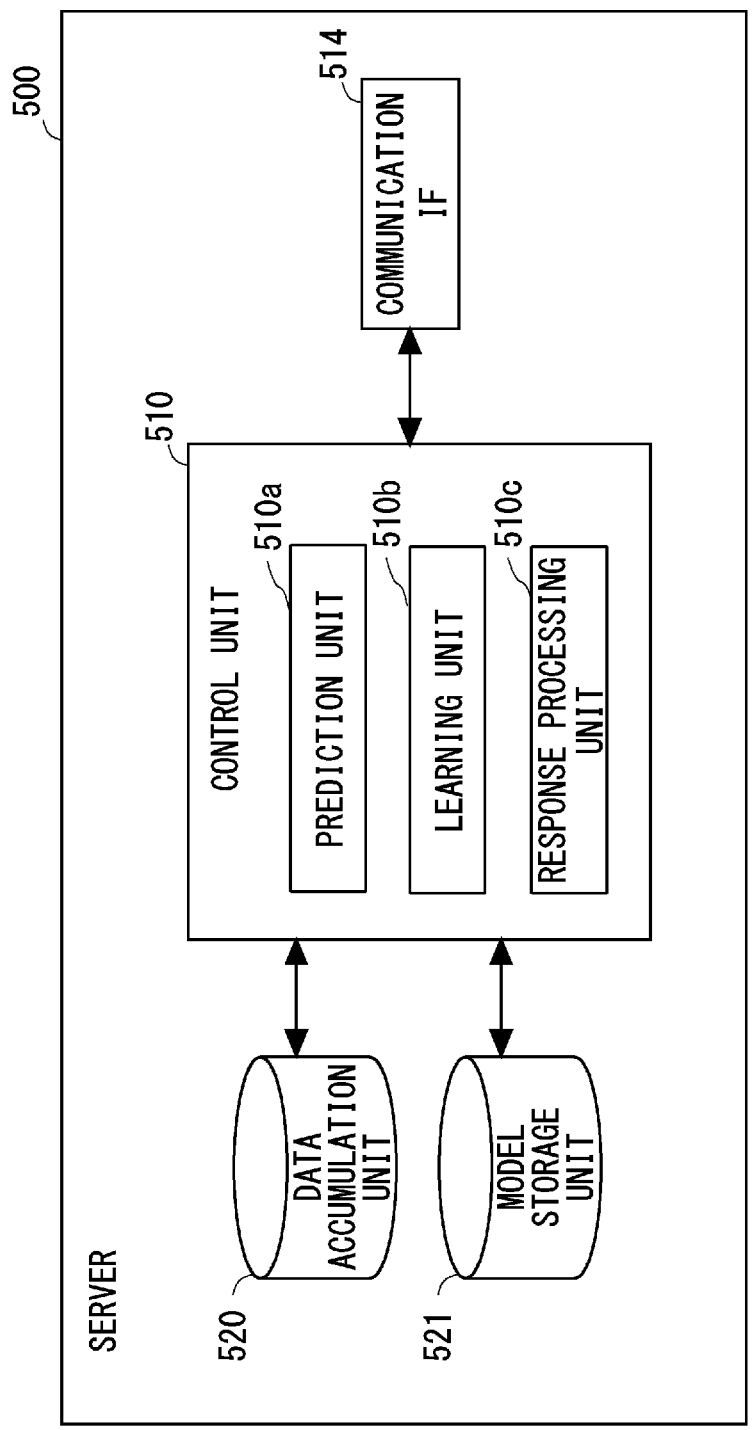
FIG. 4 is a block diagram showing an example of a configuration of a server in the rehabilitation support system shown in FIG. 1.

FIG. 4 is a block diagram showing an example of a configuration of the server 500. As shown in FIG. 4, the server 500 may include a control unit 510, a communication IF 514, a data accumulation unit 520, and a model storage unit 521. The control unit 510 is, for example, an MPU and controls the server 500 by executing a control program loaded from a system memory. The control unit 510 may include a prediction unit 510a, a learning unit 510b, and a response processing unit 510c, which will be described later. Further, in such a case, the above-described control program includes a program(s) for implementing functions of the control unit 510 including functions of the aforementioned parts 510a to 510c.

The communication IF 514 includes, for example, a wired LAN interface and is a communication interface for connecting to the network 400. The control unit 510 can receive rehabilitation data from the walking training apparatus 100 and transmit a command to the walking training apparatus 100 through the communication IF 514.

The data accumulation unit 520 includes a storage device such as an HDD (Hard Disk Drive) or an SSD (Solid State Drive) and stores rehabilitation data therein. The control unit 510 writes the rehabilitation data received from the external communication apparatus 300 into the data accumulation unit 520 through the communication IF 514.

Similarly, the model storage unit 521 includes a storage device such as an HDD or an SSD. Note that the data accumulation unit 520 and the model storage unit 521 may include (i.e., share) a common storage device. The model storage unit 521 stores at least one of a learning model that has not been trained yet (including those under training) (hereinafter referred to as an untrained model) and a learning model that has been already trained (hereinafter referred to as a trained model). When the server 500 functions as a learning apparatus, at least an untrained model is stored in the model storage unit 521. When the server 500 performs a rehabilitation support process in cooperation with the walking training apparatus 100, at least an operable trained model is stored in the model storage unit 521.

Further, the control unit 510 may be configured so as to perform control to switch between a function as a learning apparatus and a function for performing a rehabilitation support process by using a trained model. Note that the servers 500 may be distributed to (or divided into) an apparatus that is used in a learning stage and an apparatus that is used in an operation stage in which a trained model is used. The learning unit 510b is provided in order to enable the server 500 to function as a learning apparatus. Further, the prediction unit 510a and the response processing unit 510c are provided in order to enable the server 500 to perform a part of the rehabilitation support process.

(Rehabilitation Data)

Prior to describing the prediction unit 510a, the learning unit 510b, and the response processing unit 510c, rehabilitation data that the server 500 can collect for learning or for a rehabilitation support process is described hereinafter. The rehabilitation data that the server 500 can collect mainly includes (1) setting parameters of the walking training apparatus 100, (2) detection data detected by sensors and the like provided in the walking training apparatus 100, (3) data related to the trainee 900, and (4) data related to the training staff member 901. The rehabilitation data of the above-described items (1) to (4) may be collected in association with their acquisition date. Further, the detection data or the setting parameter may be collected as time-series log data, or may be, for example, feature values extracted from data acquired at certain time intervals.

The rehabilitation data is mainly data that is obtained by an input operation, an automatic input, a measurement by a sensor, or the like in the walking training apparatus 100. Further, the rehabilitation data may also include recorded image data recorded by the camera 140. Note that the rehabilitation data may be data acquired on each day of rehabilitation. In this case, the rehabilitation data can be referred to as daily report data. In the following description, it is assumed that the server 500 collects rehabilitation data generated by the walking training apparatus 100. However, it is also possible to configure the server 500 so as to acquire a part of rehabilitation data from an apparatus other than the walking training apparatus 100 such as another server. Here, the part of the rehabilitation data may be, for example, a detail of data of the above-described item (3) such as a symptom of the trainee 900, or a detail of data of the above-described item (4) such as years of experience of a PT (Physical Therapist). The former can be stored in other servers as medical record information of the trainee 900 and the latter can be stored in other servers as a personal history of a PT.

In the learning stage, the server 500 may receive rehabilitation data from the walking training apparatus 100 when new rehabilitation data is generated or at regular intervals such as on every day or in every week. The type of rehabilitation data to be used (the content included in rehabilitation data) in the learning stage may be changed from that in the operation stage. For example, in the operation stage, the server 500 may receive rehabilitation data from the walking training apparatus 100 at the start of training, and may receive data of the above-described item (1) and (2) that is changed during the training. Further, the transmission and the reception of rehabilitation data may be initiated by either the walking training apparatus 100 or the server 500.

The above-described item (1) is described.

The data of the above-described item (1) can be defined as training data of the trainee 900 that is acquired during rehabilitation in the walking training apparatus 100 together with the detection data of the above-described item (2).

The setting parameter of the walking training apparatus 100 is, for example, data that is input by an operator or automatically set in order to define the actions performed by the walking training apparatus 100. Note that as described above, it is assumed that the operator is typically the training staff member 901 who actually attends the training of the trainee 900. Therefore, the following description is given on the assumption that the operator is the training staff member 901. Further, the training staff member 901 is often a PT (Physical Therapist). Therefore, the training staff member 901 may also be referred to simply as the "PT" in the following description.

In the walking training apparatus 100, the level of difficulty of walking training can be adjusted by the setting parameters. Note that the setting parameters may include a parameter indicating the level of difficulty, and in this case, some or all of the other setting parameters may be changed according to the change in the level of difficulty. The training staff member 901 increases the level of difficulty of the walking training as the trainee 900 recovers. That is, the training staff member 901 reduces the assistance provided by the walking training apparatus 100 as the walking ability of the trainee 900 improves. Further, the training staff member 901 increases the assistance when an abnormality is found during the walking training. As the training staff member 901 appropriately adjusts the setting parameters, the trainee 900 can perform appropriate walking training and hence perform the rehabilitation more efficiently.

Specific examples of the setting parameters are shown hereinafter.

Examples of the setting parameters include a partial weight-supported amount [%], vertical positions of the handrails 130a [cm], left/right positions of the handrails 130a [cm], presence/absence of a hip joint, ankle joint plantar flexion limitation [deg], and ankle joint dorsiflexion limitation [deg]. Further, the examples of the setting parameters also include a treadmill speed [km/h], swinging assistance [level], and a swinging forward/backward ratio [forward/backward]. Further, the examples of the setting parameters also include knee extension assistance [level], a knee flexing angle [deg], a knee flexing/extending time [sec], a wedge thickness (or a shoe lift) [mm], a weight-off threshold [%], and a load threshold [%]. Further, the examples of the setting parameters also include an inclination of the belt of the treadmill [deg], assistance for a motion of a joint by the walking assistance apparatus [level], a frequency with which assistance for a motion of a joint or swinging assistance by the walking assistance apparatus is provided, a condition for determining abnormal or normal walking (e.g., a determination threshold), a condition for determining that the trainee will fall down or is likely to fall down (e.g., a determination threshold), and a condition for an occurrence of abnormal or normal walking in the case where a notification is provided in association with the abnormal or normal walking (a frequency of occurrences, an occurrence threshold, etc.). Note that the notification may be any of a sound, a vibration, a display, or the like, and may include some or all of them. Note that any type of unit may be used as the unit of data included in rehabilitation data, including the above-shown setting parameters.

The partial weight-supported amount is a ratio at which the weight of the trainee 900 is supported by making the harness pulling unit 112 pull the harness wire 111. The training staff member 901 sets the partial weight-supported amount to a lower value as the desired level of difficulty of the walking training increases. The vertical positions and the left/right positions of the handrails 130a are amounts of adjustments of the handrails 130a from reference positions. The presence/absence of a hip joint is whether or not the hip joint is attached. The ankle joint plantar flexion limitation and the ankle joint dorsiflexion limitation define an angular range in which the lower-leg frame 123 and the sole frame 124 can rotate around the hinge axis $H_b$. The ankle joint plantar flexion limitation corresponds to an upper-limit angle on the front side and the ankle joint dorsiflexion limitation corresponds to a maximum angle on the rear side. That is, the ankle joint plantar flexion limitation and the ankle joint dorsiflexion limitation are limit values of angles at which the ankle joint is bent in a direction in which the toe is lowered and a direction in which the toe is raised, respectively. The training staff member 901 sets the values of the ankle joint plantar flexion limitation and the ankle joint dorsiflexion limitation so that the angular range increases as the desired level of difficulty of the walking training increases.

The treadmill speed is a walking speed on the treadmill 131. The training staff member 901 sets the treadmill speed to a higher value as the desired level of difficulty of the walking training increases. The swinging assistance is a level corresponding to the pulling force applied by the front wire 134 when the leg is swung. Further, the maximum pulling force is increased as this level is raised. The training staff member 901 sets the swinging assistance to a lower level as the desired level of difficulty of the walking training increases. The swinging forward/backward ratio is a ratio between the pulling force by the front wire 134 and the pulling force by the rear wire 136 when the leg is swung.

The knee extending assistance is a level corresponding to the driving torque of the joint drive unit 221 that is applied to prevent the knee from buckling during the stance state. Further, the driving torque is increased as this level is raised. The training staff member 901 sets the knee extending assistance at a lower level as the desired level of difficulty of the walking training increases. The knee flexing angle is an angle at which knee extending assistance is provided. The knee flexing/extending time is a period during which the knee extending assistance is provided. Further, when this value is large, the knee is assisted so that it is slowly flexed and extended, whereas when this value is small, the knee is assisted so that it is quickly flexed and extended.

The wedge thickness is a height of a member such as a cushion provided in the sole of the shoe of the leg of the trainee 900 opposite to the paralyzed leg thereof (i.e., the leg on the side on which the walking assistance apparatus 120 is not attached). The weight-off threshold is one of the thresholds for the load (i.e., the pressure) applied to the sole. When the load becomes smaller than this threshold, the swinging assistance is cancelled (i.e., ceased). The load threshold is one of the thresholds for the load applied to the sole. When the load exceeds this threshold, the swinging assist is provided (i.e., started). As described above, the walking assistance apparatus 120 may be configured so that the flexing/extending motion of the knee can be adjusted by four setting parameters, i.e., the knee flexing angle, the knee flexing/extending time, the weight-off threshold, and the load threshold.

Further, the walking training apparatus 100 may also be configured so that setting values of various parameters such as a load and an angle, a target value, a target achievement rate, a target achievement timing, etc. are fed back to the trainee and/or training staff member by a sound output from a speaker(s) (not shown). The above-described setting parameters may include parameters for other settings such as presence/absence of a feedback sound and its volume.

Further, the above-described setting parameters may not be setting parameters directly related to the level of difficulty of the training. For example, the above-described setting parameters may be setting values for images, music, a type of game, a level of difficulty of game, etc. that are provided through the training monitor 138 or a speaker(s) (not shown) in order to motivate the trainee 900.

Note that the above-described setting parameters are merely examples and other setting parameters may be used. Further, some of the above-described setting parameters may not be used. Further, although the above-described setting parameters include many parameters for adjusting the level of difficulty of the training as described above, they may also include parameters unrelated to the level of difficulty. For example, the walking training apparatus 100 may be configured so as to display an alert icon image that is to be displayed on the training monitor 138. Further, examples of the setting parameters unrelated to the level of difficulty include parameters for increasing the degree of concentration of the trainee 900 on the training, such as the size and the displaying interval of the above-described alert icon image. Further, time information such as date and time at which the setting operation is performed or timing information other than the time (e.g., information indicating a distinction between the stance phase, the swing phase, etc. in one walking cycle) can be added to the above-described setting parameters.

The above-described item (2) is described.

The detection data of the above-described item (2) can be defined as training data of the trainee 900 that is acquired during the rehabilitation in the walking training apparatus 100 together with the data of the above-described item (1).

A typical example of the detection data is sensor data. The sensor data is sensor values detected by various sensors of the walking training apparatus 100. For example, the sensor data includes an inclination angle of the trunk detected by the posture sensor 217, a load and an inclination angle detected by the handrail sensor 218, an angle detected by the angle sensor 223, etc. The sensors that output the sensor data are an acceleration sensor, an angular-velocity sensor, a position sensor, an optical sensor, a torque sensor, a weight sensor, etc. Further, encoders provided in motors of the winding mechanisms or the like of the front wire 134, the rear wire 136, and the harness wire 111 may be used as sensors. Further, a torque sensor (a load cell) of the motor may be used as a sensor, or a current detection unit that detects a driving current value for driving the motor may be used as a sensor.

Further, the sensor data may include, for example, line-of-sight data acquired by a line-of-sight detection sensor that detects a line of sight. Similar line-of-sight data can be obtained by detecting a line of sight of the trainee 900 by performing image processing based on an image taken by shooting at least an area including the eyes of the trainee 900, or obtained by determining the orientation (upward/downward etc.) of the face of the trainee 900 based on an image taken by shooting at least the face. Such data may also be included in the aforementioned detection data. Further, the detection data may be audio data (voice data) acquired by a voice acquisition unit, such as a microphone, that acquires a voice of the trainee 900 or the training staff member 901, text data obtained by performing a voice analysis on the voice data, or data obtained by analyzing the text data. The voice of the training staff member 901 may include an encouraging talk to the trainee 900 about, for example, how to correct his/her walking. Further, the sensor data may be data obtained by detecting brain waves of the trainee 900 by using an electroencephalograph, or may be data obtained by detecting brain waves of the training staff member 901 by using an electroencephalograph.

In particular, in this embodiment, control is performed based on a motivation as will be described later. Therefore, motivation information indicating a motivation is acquired. Examples of the motivation information include camera information (information indicating the state of the trainee 900, such as a line of sight, an orientation of the head, and a facial expression) obtained by the camera 140 and information about the inclination angle of the trunk of the trainee 900 obtained by the posture sensor 217. Although the camera 140 has been described as one that takes an image of the whole body of the trainee 900, it may be positioned so as to take an image of, in particular, the line of sight or the face of the trainee 900 in order to obtain motivation information. It is considered that when the direction of the line of sight or the orientation of the head (the direction of the face)

is a downward direction (e.g., when he/she does not look at the center of the training monitor 138 but looks at the lower side thereof), his/her motivation is low. Regarding the facial expression, it is considered that, for example, when the mouth is curved (e.g., is slacken), the motivation is low. Further, information that is obtained when the trainee 900 is not performing the training can also be taken into consideration. For example, it is considered that the motivation of a trainee 900 who constantly looks downward during the preparation is low.

Further, examples of the motivation information also include information on a conversation (communication) between the training staff member 901 and the trainee 900 included in audio data acquired by an audio acquisition unit such as a microphone(s). For example, it is considered that the high/low (i.e., level) of the motivation of the trainee 900 can be estimated from his/her positive attitude for a conversation and/or the ratio of his/her speech in the conversation. Further, it is possible to obtain information indicating the level of motivation by combining the conversation with the line of sight or the like. For example, in a situation in which the trainee 900 continuously looks downward or reluctantly continues the training when the training staff member 901 talks to him/her, it can be presumed that his/her motivation is low.

Further, the line-of-sight detection sensor, a shooting unit that takes the above-described image, a microphone, and the like can be disposed in the walking training apparatus 100 itself. Alternatively, they can also be disposed in, for example, an eyeglass-type wearable terminal that is worn by the trainee 900. This terminal may include a wireless communication unit that wirelessly transmits and receives data by a wireless communication technique such as Bluetooth (Registered Trademark). Further, the walking training apparatus 100 may also include a wireless communication unit. In this way, the walking training apparatus 100 can acquire data acquired by the wearable terminal through wireless communication. Although the electroencephalograph is limited to those having high detection accuracy, it may be disposed in the walking training apparatus 100 itself and configured so that the electroencephalogram of the trainee 900 and that of the training staff member 901 can be separately detected. However, the electroencephalograph may be disposed at a position near the person whose brain waves are detected, such as being disposed in the above-described eyeglass-type wearable terminal (e.g., in a side frame of the eyeglasses).

Further, the detection unit that acquires detection data, such as a sensor, is not limited to those described above with reference to FIGS. 1 to 3 or those exemplified by the eyeglass-type wearable terminal. For example, the trainee 900 may wear clothes equipped with a wearable biosensor and/or a wearable touch sensor. Here, the clothes are not limited to those worn on the upper body. That is, they may be those worn on the lower body, a top-and-bottom set, or those attached to a part of the harness 110 or the like. Further, a wireless communication unit like the one described above is provided in each of the clothes and the walking training apparatus 100. In this way, the walking training apparatus 100 can acquire data acquired by the wearable biological sensor or the wearable touch sensor through wireless communication. The wearable biosensor can acquire vital data such as the heart rate of the wearer. The wearable touch sensor can acquire data indicating information about a touch on the trainee 900, who is the wearer, made from the outside. That is, the wearable touch sensor can acquire data indicating information about a position where the training staff member 901 touched the trainee 900.

Further, the detection data is not limited to the values indicated by the detection signals detected by various sensors and the like. That is, they may include values calculated based on the detection signals from a plurality of sensors and statistical values obtained by statistically processing detection signals from one or a plurality of sensors or the like. As the statistical values, various statistical values such as an average value, a maximum value, a minimum value, and a standard deviation value may be used. Alternatively, they may be static statistical values or dynamic statistical values over a certain period such as one day, one training practice, or one walking cycle.

For example, the sensor data may include an open angle of the knee joint calculated from the angle between the upper-leg frame 122 and the lower-leg frame 123 detected by the angle sensor 223. Further, the sensor data of the angle sensor may include an angular velocity that is obtained by differentiate the angle. The sensor data of the acceleration sensor may be a velocity that is obtained by integrating the acceleration or a position that is obtained by integrating the acceleration twice.

For example, the detection data may include the below-described average value, the sum total value, the maximum value, the minimum value, and the representative value for each day or for each rehabilitation session on one day. Here, examples of the average value include an average speed (total walking distance/total walking time) [km/h], an average value of a stride length [cm], a walking rate [steps/min] indicating the number of steps per minute, a walking PCI [beats/m], and a falling-down prevention assistance [%]. The average speed may be, for example, a value calculated from a speed setting value of the treadmill 131 or a value calculated from the drive signal in the treadmill drive unit 211. The stride length means a distance from where one heel touches the ground to where the same heel touches the ground again. The PCI means a Physiological Cost Index (a clinical indicator of a physiological cost index). The walking PCI indicates energy efficiency during the walking. The falling-down prevention assistance [%] means a rate corresponding to the number of times of falling-down prevention assistance [times] per step, i.e., the number of times the training staff member 901 has assisted the trainee 900 to prevent him/her from falling down per step. That is, the falling-down prevention assistance [%] means a rate at which falling-down prevention assistance actions are performed for each step.

Further, examples of the sum total value include a walking time [s], a walking distance [m], the number of steps [steps], the number of times of falling-down prevention assistance [times], and a falling-down prevention assistance part and the number of times for each part [times].

Further, examples of the maximum value or the minimum value include maximum values or minimum values of a continuous walking time [s], a continuous walking distance [m], the number of continuous steps [steps], and a minimum value of a walking PCI [beats/m] (in other words, a longest distance the trainee can walk per beat). Examples of the representative value include a speed of the treadmill 131 that has been used most frequently (a representative speed [km/h]).

As described above, data supplied directly or indirectly from the detection unit such as various sensors can be included in the detection data. Further, time information such as date and time at which the detection is performed or timing information other than the time can be added to the above-described detection data.

Note that the above-described detection data is merely an example and other detection data may be used. Further, some of the above-described detection data may not be used. That is, when the detection data is used as rehabilitation data, all that the server 500 has to do is to collect at least one detection data (i.e., at least one detection data from which some information indicating or related to the motivation can be obtained).

The above-described item (3) is described.

The data related to the trainee 900 (hereinafter referred to as trainee data) indicates, for example, a property of the trainee 900. Examples of the trainee data include an age, a gender, a physique (a height, a weight, etc.) of the trainee 900, information about a symptom, a Br. Stage, an SIAS, an initial walking FIM, and a latest walking FIM. Further, the trainee data may also include a name or an ID of the trainee 900. Further, the trainee data may also include preference information indicating a preference of the trainee 900 and personality information indicating his/her personality. Further, the trainee data may include, as the FIM, an exercise item other than those related to the walking ability, and may include a recognition item. That is, the trainee data may include various data indicating physical abilities of the trainee 900. Note that part or all of the trainee data may be referred to as body information, basic information, or trainee feature information.

Note that the symptom information may include information indicating an initial symptom, a time when the symptom appears, and a current symptom. Further, it can be considered that the trainee 900 needs to perform rehabilitation mainly because of at least one of the symptoms described above. However, symptoms that are unlikely to be directly related to the rehabilitation may also be included in the symptom information. Further, the symptom information may also include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/subarachnoid hemorrhage), etc.

The Br. Stage means a Brunnstrom Recovery Stage in which a recovery process of a hemiplegia is divided into six stages based on the observation. The trainee data may include, of the Br. Stage, lower-limb items that are main items related to the walking training apparatus 100. The SIAS means a Stroke Impairment Assessment Set, which is an index for comprehensively evaluating dysfunction caused by a stroke. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

The FIM (Functional Independence Measure) is one of the evaluation methods for evaluating ADL (Activities of Daily Life). In the FIM, a patient is evaluated (i.e., classified) into seven stages, i.e., one point to seven points according to the level of assistance.

For example, a walking FIM is a general index indicating the degree of recovery. A patient who can walk 50 m or longer without an assistant and without a harness (an assisting device) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee 900 gradually increases. Note that the walking distance in the evaluation of the walking FIM is not limited to 50 m. For example, the walking distance may be 15 m.

As can be understood from the above description, the latest walking FIM used by the walking training apparatus 100 is used as not only an index indicating the physical ability of the trainee 900 but also an index indicating the degree of recovery of the trainee 900 from the start of the rehabilitation. The walking FIM is used as an index indicating the moving ability of the trainee 900 when no actuator is used, i.e., an index indicating his/her walking ability. In other words, the walking FIM is an important index in order to recognize the progress of the rehabilitation of the trainee 900. Further, the amount of change from the initial walking FIM to the latest walking FIM or its changing speed is also used as an index indicating the degree of recovery. The change speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in the case where the trainee 900 is a hospitalized patient.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a wedge thickness, a used harness (e.g., with the walking assistance apparatus 120, with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

As described above, the trainee data in the above-described item (3) may include index data about rehabilitation performed by the trainee 900 by using the walking training apparatus 100, including at least one of the symptom, the physical ability, and the degree of recovery of the trainee 900. Note that in general, data that can be included in both concepts of the physical ability and the degree of recovery, such as the latest walking FIM, may be included in one of them. However, such data can also be included in both of them. Note that the same applies to all the items of the rehabilitation data. Further, data of a given item can be handled as data of one or a plurality of the above-described items (1) to (4). Further, time information such as the date and time at which the walking FIM is acquired, e.g., the measurement date of the walking FIM may be added in the above-described trainee data.

The above-described item (4) is described.

The data about the training staff member 901 (hereinafter referred to as staff data) indicates, for example, a property of the training staff member 901. The staff data includes a name or an ID, an age, a gender, a physique (a height, a weight, etc.) of the training staff member 901, a name of a hospital to which the training staff member 901 belongs, and his/her years of experience as a PT or a doctor. The staff data may include, as data related to the assistance, a value that numerically represents the timing at which the trainee 900 is assisted.

Further, in the case where a plurality of training staff members simultaneously assist the rehabilitation, the rehabilitation data may include data of the plurality of staff members. Further, each staff data may include information indicating whether the staff member is the main training staff member or an assistance training staff member. In addition to or instead of such information, each staff data may include information indicating whether the staff member is a training staff member who performs a setting operation and/or image checking in the management monitor 139, or whether or not the staff member is a training staff member who just physically supports the trainee 900 by hand.

Further, the walking training apparatus 100 may be configured so that a user (e.g., a training staff member) can enter a rehabilitation plan for the trainee 900. Further, the data of the rehabilitation plan entered as described above may also be included as staff data related to the training staff member 901 who has entered the data or as rehabilitation data belonging to other categories. Further, the walking training apparatus 100 may be configured so that, to make it possible to cope with the change of the training staff member 901, a user can enter remarks and/or messages for assisting the training of the trainee 900 in the future. Further, the data entered as described above may also be included as staff data related to the training staff member 901 who has entered the data or as rehabilitation data belonging to other categories. The reason for including these data in the rehabilitation data is that there are possible situations where a training staff member has been able to successfully carry out the training of the trainee 900 because of the presence of remarks and/or messages given by other skilled training staff members. Further, time information such as the date and time at which the rehabilitation plan is entered, e.g., the input date and time of the rehabilitation plan may be added in the above-described staff data.

(Learning Stage: Construction of Learning Model)

Figure 5:
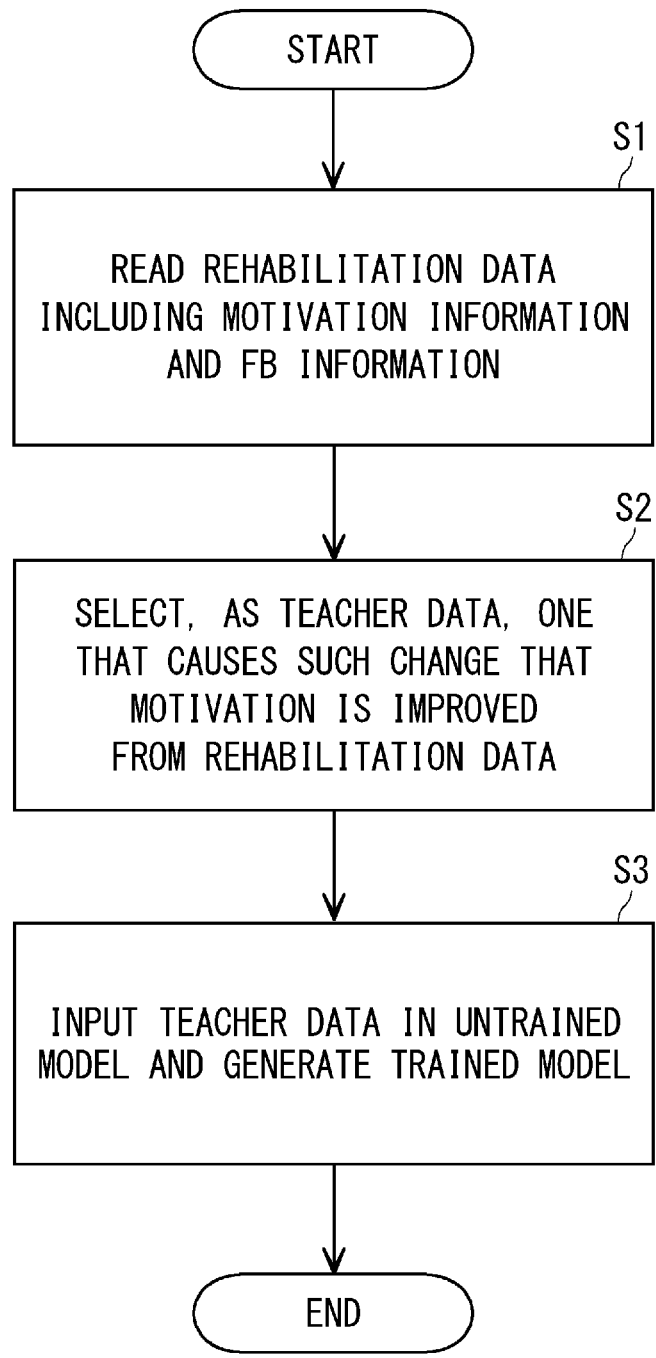
FIG. 5 is a flowchart for explaining an example of a learning process performed by the server shown in FIG. 4.

Next, processes performed in a learning stage (a learning phase) in the control unit 510 of the server 500 will be described with reference to FIGS. 5 and 6. FIG. 5 is a flowchart for explaining an example of a learning process performed by the server 500. FIG. 6 shows a table for explaining a data set for learning used (hereinafter also referred to as a learning data set) in the learning process, and shows an example of parameters that are input to or output from the learning model.

The server 500 collects rehabilitation data from a plurality of walking training apparatuses 100. Then, the server 500 accumulates the collected rehabilitation data in the data accumulation unit 520. The control unit 510 constructs a trained model from an untrained model by performing pre-processing (preliminary processing) as appropriate on part or all of the information included in rehabilitation data like the one described above and performing machine learning by using the pre-processed data. A pre-processing unit (not shown) disposed in the control unit 510 performs a pre-process (a preparatory process), and the learning unit 510b performs machine learning. Note that it is assumed that data for which the preparatory process has already been performed includes at least training data including motivation information and feedback (FB) information.

The motivation information is information indicating a motivation of the trainee 900 as described above, and may be, for example, information indicating its level (i.e., a motivation level). The motivation information may be a degree indicating a motivation, and the motivation level may be an example of the aforementioned degree. Note that although they are not specifically described, levels related to other values may also be examples of the degrees. Although the motivation level will be described hereinafter as an example of the degree indicating the motivation, this degree may be, for example, an index value based on the motivation information of the trainee 900 (i.e., an index value associated with the motivation of the trainee 900). For example, the motivation level can be determined based on this index value. The FB information is information indicating FB control that is performed based on the motivation information in the walking training apparatus 100. Examples of the FB control will be described later. Further, the trained model to be constructed is a model that inputs rehabilitation data including at least training data including motivation information and FB information as described above and predicts FB control to be performed. Needless to say, the aforementioned rehabilitation data is collected from trainings performed by a plurality of trainees 900 in the learning stage.

Firstly, a plurality of sets of data for learning (or data for its pre-processing) are prepared in the data accumulation unit 520 of the server 500. To that end, for example, the control unit 510 accumulates rehabilitation data collected in a predetermined period as one set of learning data in the data accumulation unit 520. For example, rehabilitation data collected in one walking training session or in one practice of walking training may be prepared as one set of learning data. Note that in the following description, one set of learning data is referred to as a learning data set (also referred to simply as a data set).

Note that one walking training session is a series of trainings performed by one trainee 900. Further, after one walking training session is completed by the trainee 900, the next trainee 900 performs training in the same walking training apparatus 100. One walking training session usually takes about 20 to 60 minutes. One practice of walking training is one unit during which the trainee 900 continuously walks, included in one walking training session. One walking training session includes a plurality of walking training practices. For example, one practice takes about five minutes. Specifically, in one walking training session, the trainee 900 takes a five-minute break after every time he/she performs walking training for five minutes. That is, a walking training practice and a break are alternately repeated in one walking training session. The five-minute interval between breaks is the time for one practice. Needless to say, neither of the time for one training session and the time for one practice is limited to any particular time period. That is, they may be set as appropriate for each trainee 900.

Further, rehabilitation data collected in a period shorter than the period of one practice may be prepared as one data set, or rehabilitation data collected in a period longer than the period of one practice may be prepared as one data set. Further, data obtained in a period before the training staff member 901 gives an encouraging talk or changes a setting parameter may be prepared as one data set.

An example of the data set is described with reference to FIG. 6. FIG. 6 is a table for explaining the data set. One data set contains rehabilitation data including at least training data including motivation information and FB information. In the example shown in FIG. 6, a setting parameter, line-of-sight detection data, trainee data, staff data, and FB information are associated with each other and constitute one data set. The line-of-sight detection data is data obtained by detecting line-of-sight information and is an example of the motivation information. The trainee data and the staff data are included because these information items may also affect the result.

The FB information is information indicating FB control to be performed and can be represented by a correct-answer label. Each value of correct-answer labels can be associated with a respective one of output parameters (a respective one of output nodes) of the untrained model. The FB information can include a plurality of types of data such as a notification of a motivation level "1" (among levels 0 to 9), a notification of a motivation level "2", a change in a certain setting parameter, and a change in other setting parameters. For example, these types of FB information can be provided as correct-answer labels "1", "2", "3", "4", etc., respectively. Needless to say, certain FB information used as a correct-answer label may include a plurality of different FB controls. For example, a certain correct-answer label may be a label indicating a notification of a motivation level "2" and a change in a certain setting parameter.

In the case where a notification of a motivation level is provided as the FB control, for example, a motivation level may be acquired and teacher data may be included as a correct-answer label indicating the notification and the motivation level in the data set at that moment. Further, it is also possible to obtain motivation levels to be acquired from an actual result of a questionnaire and accumulate them in advance, or obtain them from a training result (e.g., FIM efficiency and the like).

For each data set, for example, a person who makes the data set can determine which type (one or a plurality of types) of data is used as an output parameter, i.e., as the FB information in the case of the example shown in FIG. 6. Note that as can be understood from the above-described example, the setting parameter is data that can be an example of the FB information (the correct-answer label). Further, depending on the data set, there are cases where FB information (a correct-answer label) for performing FB control indicating a content described in the setting parameter is added in FIG. 6, i.e., cases where the setting parameter and the FB information in FIG. 6 are equivalent to each other.

Note that in FIG. 6, for simplifying the explanation, each of the setting parameter, the line-of-sight detection data, the trainee data, and the staff data is shown as one data (e.g., parameter_1). However, in reality, it may include a plurality of data. For example, the setting parameter may include two or more data such as a partial weight-supported amount, vertical positions of the handrails 130a, and the like. The line-of-sight detection data may include line-of-sight detection data obtained from a plurality of sensors, and/or may include motivation information other than the line-of-sight detection data in the case of the example shown in FIG. 6. The trainee data may include two or more data such as an initial walking FIM, a gender, and an age of the trainee 900. The staff data may include two or more data such as an age and a gender of the training staff member 901 as described above.

Further, as described above, the data set is not limited to raw detection data and may include data that is obtained by performing a predetermined process on detection data. For example, a feature value extracted from detection data acquired in a certain period may be used as learning data. For example, the data set may include a maximum value, a minimum value, a local maximum value, a local minimum value, an average value, etc. of detection data obtained in one practice. The control unit 510 may calculate a feature value from the detection data accumulated in the data accumulation unit 520. Alternatively, feature values may be accumulated in the data accumulation unit 520. The data accumulation unit 520 may accumulate raw data of detection data and the learning model may include a layer in which a feature value is calculated.

Needless to say, when attention is paid to only one of the data sets, there is a possibility that at least one of the motivation information and the FB information is not included in the input rehabilitation data. However, it is possible to use only the data sets each of which includes at least one of the motivation information and the FB information. Alternatively, information that is not included in the input rehabilitation data may be regarded as information indicating the same value as that of the immediately preceding information and the same value may be included (i.e., considered to be included) in the input rehabilitation. Further, the rehabilitation data may be data about rehabilitation that is performed by the trainee 900 using the walking training apparatus 100 while being assisted by the training staff member 901 as required. Therefore, an example of a data set including staff data and trainee data has been shown. This is because the motivation and the degree of change in the motivation may change according to the assistance (including communication) and/or according to the feature of the trainee.

Then, the learning unit 510b reads out the rehabilitation data including the training data including the motivation information and the FB information prepared as described above from the data accumulation unit 520 (Step S1). Next, the learning unit 510b selects, from the read rehabilitation data, rehabilitation data that is obtained when the motivation information is one that causes such a change that the motivation of the trainee 900 is improved (step S2). The processes in the steps S1 and S2 can be regarded as a pre-preprocess performed by a pre-preprocessing unit provided separately from the learning unit 510b. Note that the data set shown in FIG. 6 can be regarded as an example of data for which the process in the step S1 has already been performed. Alternatively, it can also be regarded as an example of data for which the process in the step S2 has already been performed.

Then, the learning unit 510b inputs the teacher data prepared as described above to the untrained model and thereby generates (constructs) a trained model (step S3). Note that as shown in FIG. 6, the input parameters to the untrained model include motivation information and FB information, and the output parameters from the untrained model may be FB information. As described above, the FB information is information for performing FB control, such as a motivational level for a notification and a change in a setting parameter.

Note that the type of the untrained model to be trained by the learning unit 510b and its algorithm are not limited to any particular types and algorithms. However, a neural network can be used as the algorithm and, in particular, a deep neural network (DNN) using multiple hidden layers may be used. As the DNN, for example, a feedforward (forward propagation type) neural network such as a multilayer perceptron (MLP) employing an error back propagation method can be used. Note that as described above, a publicly-known algorism can be used for the learning method used by the learning unit 510*b*, and it is briefly described hereinafter while omitting detailed description thereof.

Input parameters input to the untrained model in the learning unit 510*b* and output parameters output from the untrained model will be briefly described hereinafter by using an example in which the learning unit 510*b* generates a trained model by using the MLP. Each of the input parameters corresponds to a respective one of nodes in the input layer and each of the output parameters corresponds to a respective one of nodes in the output layer (i.e., objective variables). Each of the output data may include an index indicating FB information (including, for example, a motivation level). For example, when the motivation levels are expressed by levels 0 to 9, the number of nodes in the output layer corresponding to the notifications of the motivation levels may be ten. Note that as described above, the untrained model includes not only a completely untrained model but also a model under a learning process. Further, the trained model indicates a model that can be used for an actual operation.

When a forward propagation neural network such as the MLP is used, the learning unit 510*b* can input a data set that is obtained at the start of the rehabilitation or at each time point during the rehabilitation as one data set. However, the learning unit 510*b* can input a data set that is statistically obtained over a predetermined time as one data set at predetermined intervals. Alternatively, the learning unit 510*b* can input, as one data set, a data set statistically obtained over a predetermined period that starts from each time point (a time period longer than a unit time) at each time point. Further, in any case, one data set may be a data set that is statistically obtained over a certain period, such as over one step or over one walking cycle. In this case, the data set may be input every time the aforementioned certain period starts.

When the learning unit 510*b* generates the trained model, it inputs each of a plurality of sets of teacher data to the untrained model an appropriate number of times. For example, the learning unit 510*b* generates a trained model by using some of the sets of teacher data (training data for learning) and checks the accuracy of the generated trained model by using the remaining sets as test data. As a result of the checking, if the accuracy is satisfactory, it is implemented as it is. On the other hand, if the accuracy is poor, some process, such as changing the pre-processing or performing tuning, is performed and then the trained model is generated and evaluated again. Note that it is also possible to prepare both evaluation data for checking the accuracy and test data for testing the final accuracy in advance. Further, it is possible to generate, according to the item of the data set that is input when the trained model is generated, the trained model in which that item is taken into consideration.

Further, hyper parameters to be tuned are not limited to any particular parameters. Examples of the hyper parameters to be tuned include the number of layers of the neural network, the number of units (number of nodes) in each layer, the number of times of iterative learning using the same data set (number of epochs), and the number of input data to be passed to the model at a time (a batch size). Further, examples of the hyper parameters to be tuned include a learning coefficient and a type of an activation function. Note that the learning coefficient is also referred to as a learning rate and may be as a value for determining how much the weight of each layer is changed at a time.

Through the above-described processes, a trained model that outputs FB information indicating FB control can be constructed. In this way, as will be described later for the operation stage, in the walking training apparatus 100 using the trained model, it is possible to successively input data acquired during rehabilitation as input parameters and perform predicted (output) FB control. Therefore, it is possible to enable the training staff member 901 to assist the trainee 900 by using the FB control, i.e., to give rehabilitation support while taking the motivation of the trainee 900 into consideration.

Next, examples of other kinds of learning models will be shown. Some of the rehabilitation data may be input as image data to a feature extraction unit including, for example, a convolution layer and a pooling layer in a CNN (Convolutional Neural Network). Examples of the image data include image data that is obtained by photographing the trainee 900 so that his/her line of sight or posture can be recognized. In such a case where the feature extraction unit is provided, a result of extraction of features from the image data may be input to all the connection layers in parallel with other input parameters.

Further, as the neural network, for example, a neural network having a recursive structure such as an RNN (Recurrent Neural Network) may be used. Further, the RNN may be a neural network that is extended to include an LSTM (Long Short-Term Memory) block (also referred to simply as an LSTM). In the case of using a recursive model having the RNN, for example, one data set may include time-series data such as detection data so that the learning unit 510*b* successively inputs rehabilitation data at each time point in one practice. That is, one data set (one learning data set) may include time-series log data. Further, one data set may include feature values extracted from the log data as described above, or may include image data obtained by performing data processing on time-series detection data.

Further, when a recursive model having the RNN is used, for example, the learning unit 510*b* can input a data set statistically obtained over a predetermined time as one data set at predetermined intervals. Alternatively, even when a recursive model is used, the learning unit 510*b* can input, as one data set, a data set statistically obtained over a predetermined period that starts from each time point (a time period longer than a unit time) at each time point. Further, one data set may be a data set that is statistically obtained over a certain period, such as over one step or over one walking cycle. In this case, the data set may be input every time the aforementioned certain period starts. Note that the category of such statistical processing may include the above-described process for obtaining image data by performing data processing on time-series detection data.

In this way, it is possible to construct a trained model that outputs, in a timely manner, FB control that is predicted from the past only through the period of one data set such as the aforementioned predetermined time and the period obtained from the number of storage steps based on the current state and a past state that is a little earlier than the current state, and to use the constructed trained model in the walking training apparatus 100.

As described above, the FB information may include a setting parameter in the walking training apparatus 100 when the trainee 900 performs rehabilitation. In this way, it is possible to construct a trained model so that it can predict control related to the setting parameter as the FB control.

Further, as described above, the FB information may include the content of the notification provided in the walking training apparatus 100 when the trainee 900 performed rehabilitation. In this way, it is possible to construct a trained model so that it can predict, as the FB control, the content of the notification provided in the walking training apparatus 100 when the trainee 900 performed the rehabilitation. Note that the content of the notification may include a notification of a motivation level as described above. In this case, the walking training device 100 may be configured so as to determine the motivation level based on the motivation information and notify the training staff member 901 (or the trainee 900) of the determined motivation level.

Further, as described above, the motivation information may include at least the line-of-sight information of the trainee 900. In this way, it is possible to construct a trained model so that it can predict FB control in which the line-of-sight information of the trainee 900 is taken into consideration.

Further, as described above, the training data included in the rehabilitation data can include data that was acquired during the rehabilitation by the walking training device 100. In this way, it is possible to construct a trained model so that it can predict FB control in which the data acquired during the rehabilitation by the walking training device 100 is taken into consideration.

Further, as described above, the rehabilitation data can include trainee data indicating a feature(s) of the trainee 900. Note that examples of the features of the trainee 900 include a height, a weight, a gender, a disease, and a symptom, and the trainee data may include physical information indicating such features. In this way, it is possible to construct a trained model so that it can predict FB control in which the feature of the trainee 900 is taken into consideration. In particular, the trainee data may include symptom data indicating at least one of a disease(s) (a name(s) of a disease(s) or a disorder(s)) and a symptom(s) of the trainee 900. This is because it is expected that the FB control is changed according to the disease or the symptom of the trainee 900. The symptom data is data in which the above-described symptom information is described. In particular, in the case of walking training, examples of symptoms that are included in the symptom data include a trunk backward movement, a trunk forward bending, a trunk diseased-side movement, a knee joint flexion, difficulty of the toe-off, difficulty in keeping the swinging leg, a trunk backward bending, a pelvic retreat, a lower leg forward bending, a knee joint extension, a flexed knee joint, and swinging. Further, examples of the symptoms that are included in the symptom data include a trunk normal-side movement, vaulting, pelvic elevation, hip joint external rotation, circumduction, and a medial whip.

Further, the rehabilitation data may also include, in addition to the feature (or as a concept that is included in the feature) of the trainee 900, data indicating a preference(s) of the trainee 900 entered in the walking training device 100. In this way, it is possible to construct a trained model so that it can predict FB control in which the preference of the trainee 900 is taken into consideration.

Further, the control unit 510 may further include an extraction unit that extracts, from rehabilitation data of a plurality of trainees, rehabilitation data of a trainee whose state indicated by index data at an early stage of the training (i.e., initial data) is at a predetermined level (i.e., is a predetermined state). This extraction unit can be formed as a part of the pre-processing unit or included in the learning unit 510b, and can be configured, for example, to perform a process such as stratification according to the initial symptom. Further, the learning unit 510b generates a learning model for a trainee at a predetermined level by using rehabilitation data extracted by the extraction unit as an input. In this way, it is possible to construct a trained model so that it can predict FB control for a trainee whose index data at the early stage of the training is at a predetermined level.

Further, the above-described extraction unit may be configured to extract rehabilitation data of the following trainee 900. That is, this trainee 900 means a trainee 900 of which a combination of index data at an early stage of the training and index data at the time when it is at the predetermined level (i.e., index data at a stage at which rehabilitation data is extracted, such as index data at the current stage) is a predetermined combination. In this way, it is possible to construct a trained model so that it can predict FB control for a trainee of which the index data at the early stage of the training and the index data at the current stage constitute a predetermined combination.

(Operation Stage: Use of Learning Model)

Next, processes performed in the operation stage (the inference phase) in the walking training apparatus 100 and the server 500 will be described. As described above, the walking training apparatus 100 is configured so as to be able to access a trained model, so that it can use the trained model. Note that the trained model may also be referred to as a trained module. In the operation stage, in general, the walking training apparatus 100 and the server 500 connected thereto cooperate with each other. That is, they serve as a rehabilitation support system and perform a rehabilitation support process.

In order to operate the above-described trained model, the walking training apparatus 100 mainly includes a prediction acquisition unit and a feedback (FB) unit as described below, and the server 500 may include a prediction unit 510a and a model storage unit 521 in which the trained model is stored.

The prediction acquisition unit of the walking training apparatus 100 may include an information acquisition unit that acquires rehabilitation data including information serving as an input parameter, and a prediction result acquisition unit that obtains an output result (a result indicating FB control) from the trained model as an output parameter.

The information acquisition unit can be exemplified by, for example, the camera 140 (a camera that can mainly take an image of a line of sight), the image processing unit 216, and the posture sensor 217. Note that examples of the information acquisition unit and information acquired by the information acquisition unit are the same as those described above for the detection data of the above-described item (2). Examples of the detection data that can be detected as motivation information include data indicating a facial expression (an emotion) and conversation data as well as the line-of-sight data as described above. The information acquisition unit can acquire, as an input parameter(s), rehabilitation data including at least training data including motivation information and FB information indicating FB control for the trainee 900 who starts or is performing the training. Note that depending on the timing at which rehabilitation data is acquired, the rehabilitation data includes neither the motivation information nor the FB information. In such a case, various techniques such as those described for the one data set input to the untrained model in the learning stage can be adopted. For example, such rehabilitation data including no motivation information and no FB information may be prevented from being input to the trained model. Further, the prediction result acquisition unit can be exemplified by the input/output control unit 210c and the input/output unit 231.

The prediction unit 510a of the server 500 inputs rehabilitation data for the trainee who starts or is performing the training to the trained model and obtains a result of a prediction of FB control to be performed therefrom. Therefore, the prediction unit 510a inputs rehabilitation data to the trained model stored in the model storage unit 521 through the response processing unit 510c, operates the trained model, and inputs a necessary part of the rehabilitation data or the whole rehabilitation data to the trained model as an input parameter(s). The prediction unit 510a transmits an output parameter (data indicating an output result) output from the trained model to the walking training apparatus 100 through the response processing unit 510c. Note that the response processing unit 510c communicates with the walking training apparatus 100 through the communication IF 514.

The prediction result acquisition unit of the walking training apparatus 100 acquires, from the server 500 side, an output result (a result indicating FB control) output from the trained model as an output parameter(s). The FB unit of the walking training apparatus 100 performs FB control obtained by the prediction result acquisition unit. Further, the FB control is often control that requires an operation (e.g., an operation for changing a setting) based on the determination of the training staff member 901 in the case of the walking training apparatus 100. That is, a typical example of the FB control is a notification to the trainee 900 by the training monitor 138 or a notification to the training staff member 901 by the management monitor 139. Therefore, the above-described FB unit may include a notification control unit 210d, and may also include the display control unit 213, the management monitor 139, the training monitor 138, an audio control unit (not shown), a speaker(s), and so on.

In this way, when the trainee 900 performs rehabilitation using the walking training apparatus 100, the training staff member 901, who assists the trainee 900, can give rehabilitation support while taking the motivation of the trainee 900 into consideration.

Further, the prediction unit 510a may reduce a weight of information (information including motivation information) acquired in a predetermined period after a setting parameter in the walking training apparatus 100 is changed. For example, the weighting is reduced in a period in which the speed of the treadmill 131 changes. This is because a trainee 900 often feels as if the training becomes difficult immediately after a setting is changed, and hence his/her motivation often changes. Therefore, the weighting is reduced in order to cope with such situations. The process for reducing a weight can be performed by the prediction unit 510a or the information acquisition unit of the walking training apparatus 100 as a pre-process before the data is input to the trained model. Alternatively, the process for reducing the weight can be carried out simply by including the setting parameter in the input parameter in the learning stage and also including the setting parameter in the input parameter in the operation stage.

Further, the above-described information acquisition unit may separately acquire, as motivation information, information in a period during which the trainee is performing the rehabilitation and information in a period other than the period during which the trainee 900 is performing the rehabilitation (i.e., during a preparation or a break). Further, the above-described information acquisition unit may separately acquire information during the preparation and information during the break. It is expected that the motivation changes depending on the period. Therefore, the acquisition unit may separately acquire information in order to cope with such changes.

Further, in this case, the prediction unit 510a or the above-described information acquisition unit may be configured so as to change the weighting of the motivation information according to the above-described period. The process for changing the weight can be carried out by the prediction unit 510a or the above-described acquisition unit as a pre-process before the data is input to the trained model. Alternatively, the processing for changing the weight can be substituted (i.e., carried out) by including period information (information indicating that it is during rehabilitation, during a preparation, during a break, etc.) in the input parameter in the learning stage and also including the period information in the input parameter in the operation stage.

In this way, for example, it is possible to perform a process in which the weight of information acquired during a period other than the rehabilitation-performing period (i.e., during a preparation or a break) is increased, and/or a process in which the weight of information acquired during a preparation is changed from that of information acquired during a break. In particular, during a preparation or a break, the training staff member 901 is often in a period in which he/she has a conversation with the trainee 900. Further, the training staff member 901 talks with the trainee 900 about the state of the training performed by the trainee 900 more often during a break than during a preparation. In reality, assuming that the period of the walking training is one hour per day, the actual walking time may be, for example, 20 minutes, and the training staff member 901 and the trainee 900 often have conversations during the remaining period, i.e., during the preparation and the break. Accordingly, it is useful (or meaningful) to separate these periods from each other and perform a process for changing a weight based on the separated period. Further, the level of a motivation may be distinguished from the degree of tiredness. For example, information about them may be observed in a time-series manner and the weight may be reduced as the training proceeds.

Figure 7:
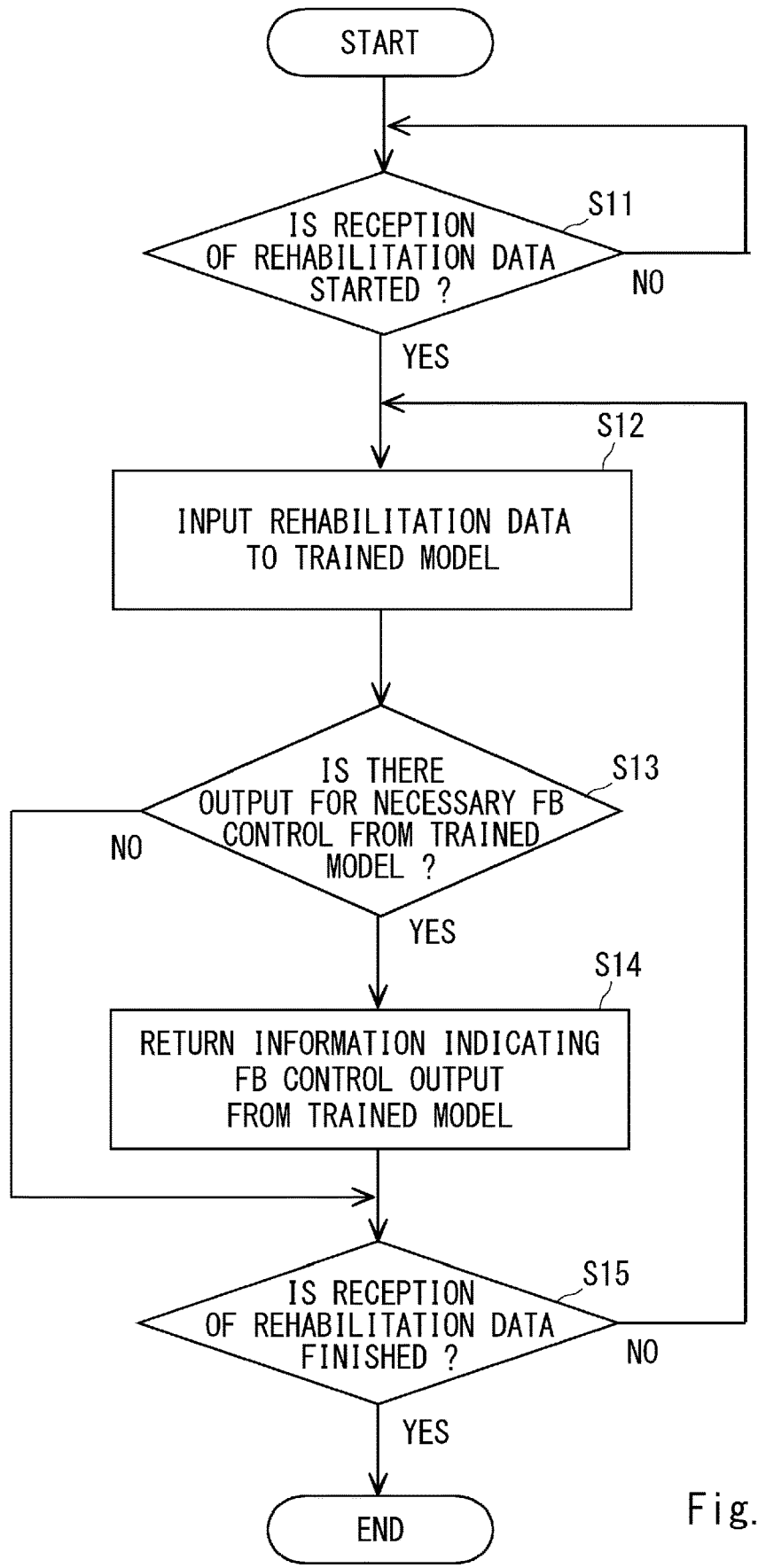
FIG. 7 is a flowchart for explaining an example of a rehabilitation support process performed in the rehabilitation support system shown in FIG. 1.

An example of the rehabilitation support process performed in the rehabilitation system including the walking training apparatus 100 and the server 500 will be described in a concrete manner with reference to FIG. 7 and the like. FIG. 7 is a flowchart for explaining an example of the rehabilitation support process performed in the server 500.

Firstly, the input/output control unit 210c of the walking training apparatus 100 outputs acquired rehabilitation data that could serve as an input parameter to the server 500 through the input/output unit 231. When the response processing unit 510c of the server 500 receives this data through the communication IF 514 (Yes at step S11), it starts a response process. The response processing unit 510c passes the received data to the prediction unit 510a. The prediction unit 510a analyzes the data, divides it into a plurality of item data, and outputs each of the item data as a respective one of input parameters in the input layer in the trained model stored in the model storage unit 521 (step S12).

The prediction unit 510a performs calculation by operating the trained model and determines whether or not there is an output for necessary FB control by determining (i.e., examining) each output parameter from the output layer (step S13). Each of the output parameters corresponds to a respective one of FB controls (which may be FB control in which a plurality of types of controls are combined). Further, the determination of the output parameters can be made by performing a process by using thresholds each of which is prepared for a respective one of the values of the output parameters in advance (or by using a common threshold). Needless to say, in the case of a model whose output parameter can have only two values, i.e., values 0 and 1, all that has to be performed is to determine whether the output parameter is 0 or 1.

In the case of Yes at the step S13, the prediction unit 510*a* passes the information indicating the FB control output from the trained model as the output parameter to the response processing unit 510*c*. Then, the response processing unit 510*c* returns this information to the walking training apparatus 100 side through the communication IF 514 (step S14). The returned information may be a command to the walking training apparatus 100. In the case of No at the step S13, the prediction unit 510*a* proceeds to a step S15 (which will be described later) without going through the step S14.

As described above, in the steps S13 and S14, the prediction unit 510*a* performs calculation by operating the trained model, and the response processing unit 510*c* generates, for an output parameter(s) output as a value for which FB control is required among the output parameters from the output layer, a command corresponding to the output parameter(s). Meanwhile, the prediction unit 510*a* does not perform any particular process for the other output parameters. That is, in some cases, the response processing unit 510*c* does not output any command at all depending on the calculation result. Such cases correspond to situations where no FB control is necessary. Note that the command can be generated by, for example, having the response processing unit 510*c* read (i.e., select) a command corresponding to the output parameter from a group of commands stored in advance. Each of the output parameters (each of the output nodes) of the trained model may be associated with a command including a content indicating FB control in advance. Further, the command may simply indicate information indicating the output parameter (e.g., information indicating the ordinal position of the node in the output layer), as long as the command can be interpreted on the walking training apparatus 100 side. The response processing unit 510*c* transmits the generated command to the walking training apparatus 100 side through the communication IF 514.

After the process in the step S14, the response processing unit 510*c* determines whether or not the reception of the rehabilitation data has been completed (step S15). Then, when the reception has been completed, the response processing unit 510*c* finishes the process, whereas when the reception has not been completed, it determines that the rehabilitation is in progress and returns to the step S12. In the case of No at the step S13, the process also proceeds to the step S15.

In the walking training apparatus 100, the input/output control unit 210*c* receives the command transmitted in the step S14. Then, for example, when the command is one that requires a notification, the input/output control unit 210*c* passes the command to the notification control unit 210*d*. The notification control unit 210*d* performs notification control corresponding to this command for the display control unit 213 or an audio control unit (not shown). Notification controls each of which corresponds to a respective one of the commands in the command group that could be transmitted from the server 500 side may be stored in the notification control unit 210*d* in advance. For example, the notification control unit 210*d* makes the display control unit 213 output, to the management monitor 139, a display control signal for displaying, for example, an image corresponding to the command on the management monitor 139.

For example, the notification control unit 210*d* makes the aforementioned audio control unit output, to a speaker(s), an audio control signal for outputting a sound corresponding to the command from the speaker(s). Note that some suggestions such as a suggestion of assistance with bare hands may be given by displaying a still image or moving images for explaining an assisting method.

Further, when the command is unrelated to the notification, the input/output control unit 210*c* may pass the command to a part corresponding to its FB control. However, as described above, in the walking training apparatus 100, the FB control is often control that requires an operation (e.g., an operation for changing a setting) based on the determination of the training staff member 901. In such a case, the command may be, for example, a command indicating a notification of an operation for changing a setting.

Through the above-described processes, in the walking training apparatus 100, FB control can be performed by using acquired data as an input parameter, and the training staff member 901 can assist the trainee 900 by effectively using the FB control. Further, since the trained model exists in the server 500, a plurality of walking training apparatuses 100 can be operated by using the common trained model.

Figure 8:
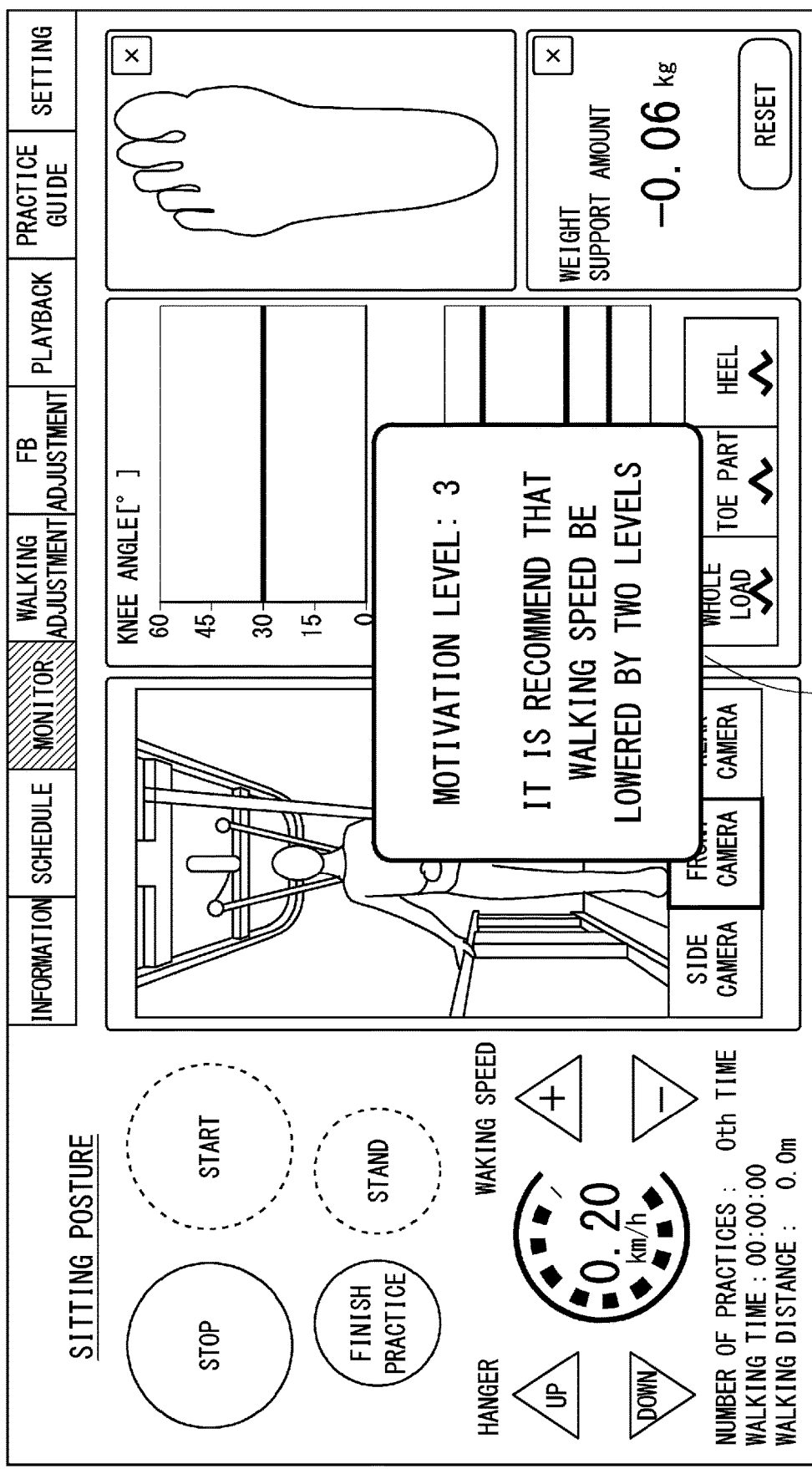
FIG. 8 shows an example of an image presented to a training staff member in the rehabilitation support process shown in FIG. 7.
Figure 9:
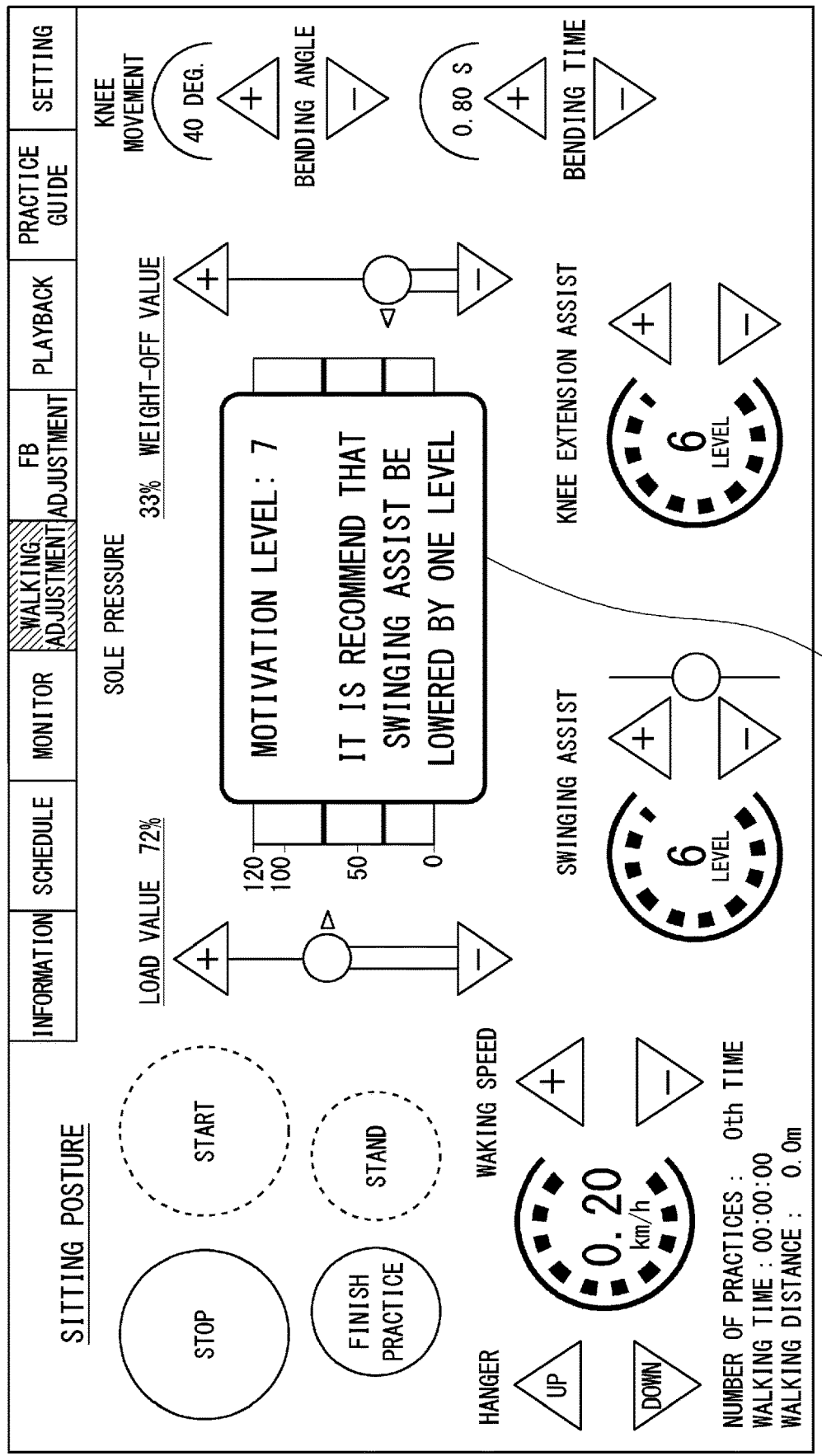
FIG. 9 shows another example of an image presented to a training staff member in the rehabilitation support process shown in FIG. 7.
Figure 11:
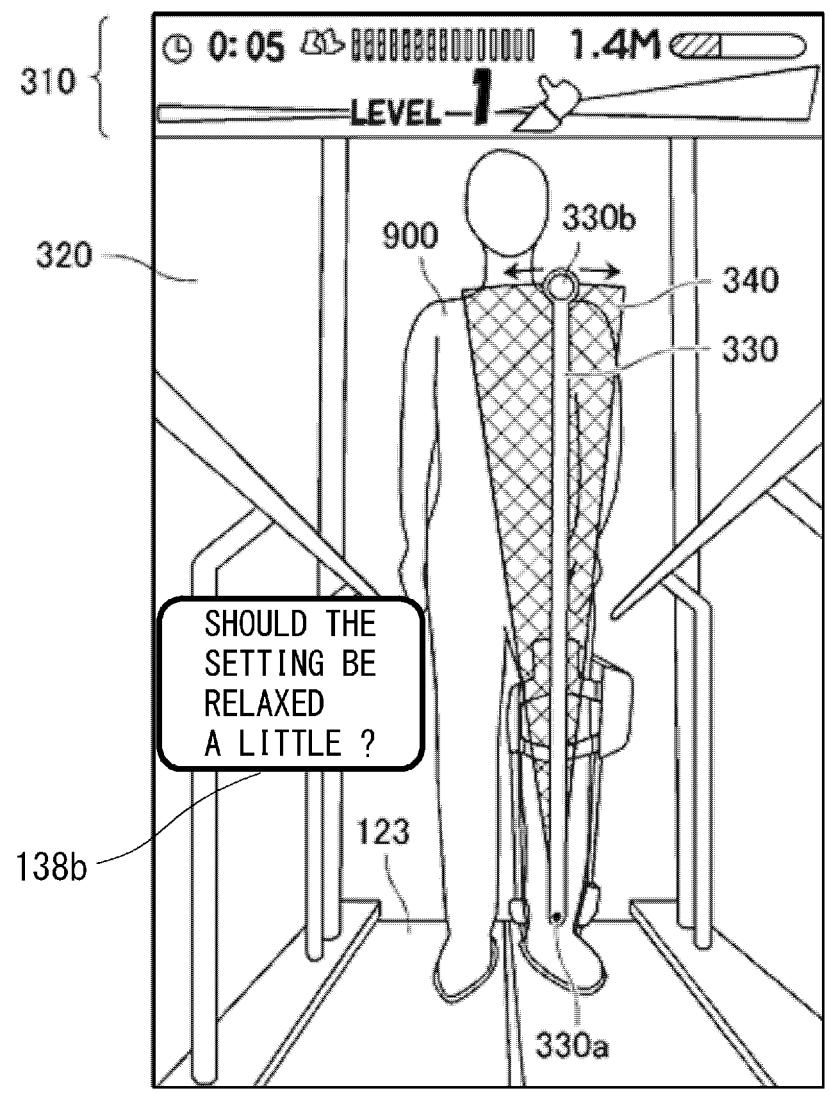
FIG. 11 shows an example of an image presented to a trainee in the rehabilitation support process shown in FIG. 7.

Next, an example of feedback performed in the FB unit exemplified by the notification control unit 210*d* and the like will be described with reference to FIGS. 8 to 11 and the like. FIGS. 8 to 10 show examples of images presented to the training staff member 901 in the rehabilitation support process shown in FIG. 7, and FIG. 11 shows an example of an image presented to the trainee 900 in the rehabilitation support process shown in FIG. 7.

The FB unit may include a first notification unit that notifies a motivation level to the training staff member 901 who assists the trainee 900. This first notification unit can be exemplified by the notification control unit 210*d* and the management monitor 139. That is, a value or a mark indicating the motivation level may be included in a GUI (Graphical User Interface) image displayed on the management monitor 139.

In a GUI image 139*a* shown in FIG. 8, a pop-up image 139*b* is superimposed on an image displayed on the management monitor 139 during the rehabilitation. The pop-up image 139*b* is displayed when the walking training apparatus 100 receives, from the server 500, a command indicating that a notification indicating that the motivation level is "3" among the levels 0 to 9 should be provided. When the motivation level is "3", the notification control unit 210*d* displays this information and suggests that the walking speed be lowered by two levels. It is assumed that a notification of this suggestion is also included in the above-described command. As described above, for example, the notification control unit 210*d* can also propose to lower the speed of the treadmill 131 (lower the level of difficulty and thereby increase an achievement rate) in order to recover the state in which the motivation level has decreased below a certain threshold. Further, each of the motivation levels may be displayed in a different color. Note that the image on which the pop-up image 139*b* is superimposed is an image that is displayed immediately before the above-described feedback, and the content included in that image is not limited to any particular contents.

In a GUI image 139*c* shown in FIG. 9, a pop-up image 139*d* is superimposed on an image displayed on the management monitor 139 during the rehabilitation. The pop-up image 139*d* is displayed when the walking training apparatus 100 receives, from the server 500, a command indicating that a notification indicating that the motivation level is "7"

among the levels 0 to 9 should be provided. When the motivation level is "7", the notification control unit 210*d* displays this information and suggests that the swinging assistance level be lowered by one. It is assumed that a notification of this suggestion is also included in the above-described command. Further, each of the motivation levels may be displayed in a different color. Note that the image on which the pop-up image 139*d* is superimposed is an image that is displayed immediately before the above-described feedback, and the content included in that image is not limited to any particular contents.

Further, the above-described first notification unit can also be formed by a speaker(s) and an audio control unit that performs control so as to output a voice or a sound through the speaker(s) (not shown), and can output a voice or a sound indicating the value of the motivation level from the speaker(s). However, the aforementioned speaker(s) may be, for example, a wireless earphone(s) (e.g., a bone-conduction-type earphone(s)) attached to an ear(s) or the like of the training staff member 901 in order to prevent the trainee 900 from hearing the sound or the voice. Needless to say, the first notification unit may be configured so as to output a voice or a sound in addition to displaying an image.

Further, as shown in the examples of suggestions for changing the level shown in FIGS. 8 and 9, the FB unit may include a second notification unit that notifies, when a command received from the server 500 includes information urging the training staff member 901 to change a setting parameter in the walking training apparatus 100, the training staff member 901 of that information. The setting parameter may be, for example, only a parameter indicating the degree of difficulty, or may be any of the parameters of the above-described item (1). The second notification unit can be exemplified by the notification control unit 210*d* and the management monitor 139, and can also be exemplified by an audio control unit and a speaker(s). In the latter case, in particular, a configuration in which the trainee 900 is prevented from hearing the voice or the sound as described above may be adopted. Needless to say, each of the second notification unit and later-described third to sixth notification units may also be configured so as to output a voice or a sound in addition to displaying an image.

Further, as shown in the examples of suggestions for changing the level shown in FIGS. 8 and 9, the FB unit may include a third notification unit that notifies the training staff member 901 of information urging him/her to change a setting parameter when the motivation level, of which the training staff member 901 is notified, changes beyond a predetermined range. In the case of this example, no suggestion is included in the received command and a suggestion is made on the FB unit side. The setting parameter may be, for example, only a parameter indicating the degree of difficulty, or may be any of the above-described various parameters. Further, the change beyond the predetermined range may mean, for example, a change in the motivation level in which the motivation level, which is in the range of the levels 0 to 9, has changed from the previous value or from a value of a predetermined period earlier by three levels or more. The third notification unit can be exemplified by the notification control unit 210*d* and the management monitor 139, and can also be exemplified by an audio control unit and a speaker(s). In the latter case, in particular, a configuration in which the trainee 900 is prevented from hearing the voice or the sound as described above may be adopted.

Further, the FB unit may also include a fourth notification unit that notifies the training staff member 901 assisting the trainee 900 of a type of conversation corresponding to the motivation level of which the training staff member 901 is notified (hereinafter also referred to as the notified motivation level). This fourth notification unit can be exemplified by the notification control unit 210*d* and the management monitor 139. In the case of this example, this notification is not included in the received command and only the notification of the motivation level is included in the received command. Further, a notification for urging the training staff member 901 to have a conversation is provided on the FB unit side. Note that, as an alternative example, the notification for urging the training staff member 901 to have a conversation can also be performed by including it in the received command as one of FB controls. Although the notification for urging the training staff member 901 to have a conversation is not shown in the drawings, for example, a sentence for urging the training staff member 901 to have a conversation may be shown in a pop-up image similar to the pop-up image 139*b* shown in FIG. 8. Regarding the sentence, when the motivation level is four or lower among the levels 0 to 9, for example, a sentence "Please propose to relax the setting a little" may be shown. Further, when the motivation level is five or higher, a sentence "Please encourage the trainee to continue at the current pace" may be shown. Needless to say, the sentence is not limited to these examples. Further, the fourth notification unit may be exemplified by an audio control unit and a speaker(s). However, in this case, in particular, a configuration in which the trainee 900 is prevented from hearing the voice or the sound as described above may be adopted.

Further, the FB unit may also include an accumulation unit that accumulates data indicating changes of the notified motivation level over time in a log, and a fifth notification unit that notifies the training staff member 901 of the log. The accumulation unit may include, for example, a storage device such as an HDD or SSD disposed in or connected to the overall control unit 210 as its accumulation area. This fifth notification unit can be exemplified by the notification control unit 210*d* and the management monitor 139.

A GUI image 139*e* shown in FIG. 10 is an image that is displayed (i.e., superimposed) by selecting a predetermined button on the image that is displayed on the management monitor 139 during the rehabilitation. Needless to say, the GUI image 139*e* may be displayed as a pop-up image like those shown in FIGS. 8 and 9. The GUI image 139*e* includes a calendar in which motivation levels, which are expressed by levels 0 to 9, of the trainee 900 performing the training are shown in respective dates. Further, a change in the level within one day may be expressed by an arrow indicating, for example, a change from "3" to "1".

Even the motivation of the same trainee 900 may increase or decrease day by day. In particular, the motivation of a trainee 900 who simultaneously develops a depressed state and a manic state drastically changes. However, by the above-described display of the calendar, the training staff member 901 can keep track of the changes in the motivation of the trainee 900. Further, each of the motivation levels may be displayed in a different color. Further, the displayed calendar is not limited to the above-shown example. For example, the calendar may be a weekly calendar, a calendar on a multi-week basis, or a calendar on a multi-month basis.

Needless to say, the check of the motivation level is not limited to those using the display of calendars. By the accumulation and the notification of the log as described above, the training staff member 901 or the like can peruse (or browse) the accumulated data in the log and make a training plan for the trainee 900 based on the log. Further, the fifth notification unit may be exemplified by an audio control unit and a speaker(s). However, in this case, in particular, a configuration in which the trainee 900 is prevented from hearing the voice or the sound as described above may be adopted.

Further, the FB unit may also include a sixth notification unit that notifies the trainee 900 of information corresponding to the notified motivation level. This sixth notification unit can be exemplified by the notification control unit 210d and the training monitor 138.

In a GUI image 138a shown in FIG. 11, a pop-up image 138b is superimposed on the image that is displayed on the training monitor 138 during the rehabilitation. The pop-up image 138b may be displayed when, for example, the notified motivation level is four or lower among the levels 0 to 9, and may include a sentence for raising the motivation such as a sentence "Should the setting be relaxed a little?". Further, for example, when the notified motivation level is five or higher, the pop-up image may include a sentence for encouraging the trainee to maintain the current state, such as a sentence "Please keep working hard at the current pace". Needless to say, the sentence is not limited to these examples. Further, the sixth notification unit can also be exemplified by an audio control unit and a speaker(s). Such a configuration is advantageous because it is possible to notify the trainee 900 by a voice or a sound even in a situation in which, for example, the motivation of the trainee 900 is low and he/she looks downward.

Note that the image on which the pop-up image 138b is superimposed is an image that is displayed immediately before the above-described feedback, and in principle, the content included in that image is not limited to any particular contents. Note that as the GUI image 138a, an example of an image that is shown when the gait of the trainee 900 is normal is shown.

A status area 310 is provided in the uppermost part of the GUI image 138a, in which status information in a training trial is displayed. The status information includes a duration of the trial, a walking distance, a training level, a score indicator, and so on. The duration of the trial is a time from the start of the trial and is measured by a timer (not shown). The walking distance is measured (i.e., calculated) based on a cumulative amount of rotations of the belt 132 rotated by the treadmill drive unit 211. The training level indicates the level of difficulty of the training trial and is updated every time it meets a predefined criterion. The level of difficulty of the training trial is defined by the rotational speed of the belt 132 and the amount of assistance by the walking assistance apparatus 120. The training level at the start of the training is set by the training staff member 901, who is a therapist or the like, according to the state of the trainee 900. The score indicator is increased or decreased according to the addition or the subtraction of the acquired points.

A camera image 320 is embedded and displayed in an area of the GUI image 138a other than the status area 310. The camera image 320 is an image of the whole body of the trainee 900 taken by the camera 140 and is displayed as, for example, real-time images having a frame rate of 60 fps. The trainee 900 can check his/her appearance during the training trial as real-time images. Note that since the trainee 900 faces the training monitor 138, the camera image 320 may be inverted in the left/right direction for easier visual recognition as shown in the figure.

Each of a trunk line 330 corresponding to the inclination of the trunk of the trainee obtained by calculation or the like and a swinging index 340 indicating a range in which swings of the trunk line 330 are allowed is superimposed on the camera image 320 as a CG (Computer Graphics) image. In this example, the trunk line 330 is represented by a CG image having a straight-pole shape extending from a base point 330a near the heel of the diseased leg of the trainee 900 to a point near the shoulder thereof. The end point 330b near the shoulder is depicted somewhat in a decorated manner so that the swings of the trunk can be visually recognized with ease.

When the trainee 900 stands upright on the belt 132, the trunk line 330 is drawn perpendicular to the surface of the belt 132 from the base point 330a to the end point 330b. Further, when the trunk of the trainee 900 swings as he/she walks, the trunk line 330 swings around the base point 330a according to the angle of the inclination. Note that since the base point 330a is set at a place near the heel of the diseased leg, the whole trunk line 330 moves according to the movement of the diseased leg (e.g., according to whether the diseased leg is in a stance state or a swing state). For the trainee 900 performing the walking training, the inclination of the trunk, which is regarded as a bad condition, is mainly caused by the state of the diseased leg. Therefore, by depicting the trunk line 330 while using the point near the heel of the diseased leg as the base point, the depicted trunk line 330 satisfactorily agrees with the feeling in regard to the recognition of the relation of cause and effect. Further, by depicting the trunk line 330 from the point near the heel to the point near the shoulder, the trunk line 330 is depicted as a relatively large object in the display area of the training monitor 138, thus improving the visibility.

The swinging index 340 is depicted in a fan-shape with its pivot being the base point 330a of the trunk line 330. The arc part of the fan-shape is depicted so as to extend along the swinging direction of the end point 330b of the trunk line 330. Further, the central angle of the fan-shape is determined according to the range in which the swings of the trunk line 330 are allowed. The swinging index 340 may be depicted in, for example, a semitransparent manner in which the swinging index 340 is lightly colored. By depicting the swinging index 340 in the semitransparent manner, the image of the trainee 900 is not significantly hidden by the swinging index 340. Therefore, the trainee 900 can check his/her own state more accurately. The range in which the swings are allowed is defined in advance for each training level. The range is set to a wide range when the training level is low, and is gradually narrowed as the training level rises.

By depicting the swinging index 340 as a fan-shape as described above, the trainee 900 can recognize that his/her gait is one that is allowed in the training trial when the trunk line 330, which swings according to the moving leg, remains inside the fan-shape. Note that the trainee 900 can recognize whether the current inclination of the trunk is within the allowable range by, for example, just observing whether the end point 330b is located on the fan-shaped arc without closely observing the whole trunk line 330. The above-described depiction is convenient for the trainee 900, who frequently looks at the assistant and/or at his/her feet during the training trial.

(Effect)

As described above, according to this embodiment, it is possible to generate a trained model described below. That is, the trained model is a model that predicts FB control that enables, when a trainee 900 performs rehabilitation using the walking training apparatus 100, a training staff member 901 who assists the trainee 900 to give rehabilitation support while taking a motivation of the trainee 900 into consideration.

Further, according to the walking training apparatus 100 in accordance with this embodiment, since it is possible to access the trained model generated as described above, it is possible to give rehabilitation support by using the trained model. For example, according to this embodiment, the training staff member 901 can give rehabilitation support by changing a setting or giving an encouraging talk while making a determination based on the notified motivation level of the trainee 900 and/or based on a suggestion for changing a setting or for giving an encouraging talk. In particular, as shown in FIG. 1, in the case of the walking training apparatus 100, since the training staff member 901 often stands behind the trainee 900, it is impossible to directly observe the facial expression of the trainee 900 and hence impossible to infer the motivation of the trainee 900. However, in this embodiment, it is also possible to configure the walking training apparatus 100 so that the training staff member 901 recognizes the motivation level, and thereby to enable the training staff member 901 to give rehabilitation support according to the motivation.

(Supplemental Remarks on Method and Program)

As can be understood from the above-described description, in this embodiment, it is also possible to provide a learning method including a learning step described below. In the learning step, rehabilitation data about rehabilitation performed by a trainee 900 using the walking training apparatus 100, which performs FB control based on the motivation information of the trainee 900, is input and a learning model that predicts the FB control to be performed is generated. The aforementioned rehabilitation data includes at least training data including motivation information of the trainee 900 and FB information indicating the FB control. Further, in the learning step, the learning model is generated by using, as teacher data, the aforementioned rehabilitation data that is obtained when the motivation information is one that causes such a change that the motivation of the trainee 900 is improved.

In this embodiment, as can be understood from the above description, it is also possible to provide a method for supporting rehabilitation (a method for operating the walking training apparatus 100) in the walking training apparatus 100 capable of accessing the trained model, i.e., the learning model trained by the above-described learning method. Further, this method includes an acquisition step and an FB step described below. In the acquiring step, rehabilitation data of a trainee who starts or is performing training is input to the trained model and a result of a prediction of FB control to be performed is obtained. In the FB step, the FB control obtained in the acquisition step is performed.

In this embodiment, as can be understood from the above-described description, it is also possible to provide a program (a learning program) for causing a computer to perform the above-described learning step. Further, in this embodiment, needless to say, it is also possible to provide a trained model trained by the learning apparatus, a trained model trained by the learning method, and a trained model trained by the learning program. Further, in this embodiment, as can be understood from the above-described description, it is also possible to provide a rehabilitation support program for causing a computer of the walking training apparatus 100 capable of accessing the above-described trained model to perform the above-described acquisition step and FB step.

Second Embodiment

In the first embodiment, an example in which the server 500 includes the learning unit 510b and the server 500 generates a trained model is described. In contrast, in this embodiment, the learning unit and the pre-processing unit are provided on the walking training apparatus 100 side (e.g., in the overall control unit 210). A rehabilitation support system according to this embodiment needs to include only the walking training apparatus 100. However, in this case, it is desirable to configure the rehabilitation support system so that it can collect rehabilitation data from other walking training apparatuses in order to increase the amount of rehabilitation data collected in the learning stage.

Further, in the first embodiment, regarding the operation stage, an example in which the trained model is provided in the server 500, and the walking training apparatus 100 transmits rehabilitation data to the server 500 and receives its response from the server 500 is shown. However, the present disclosure is not limited to such examples. For example, the trained model may be incorporated on the walking training apparatus 100 side (e.g., in a storage unit disposed in the overall control section 210). Therefore, the walking training apparatus 100 may include a storage unit that stores the trained model. Further, although it is not specifically described, the various examples described above in the first embodiment can also be applied to this embodiment and the same effects as those in the first embodiment can be achieved.

Third Embodiment

Figure 12:
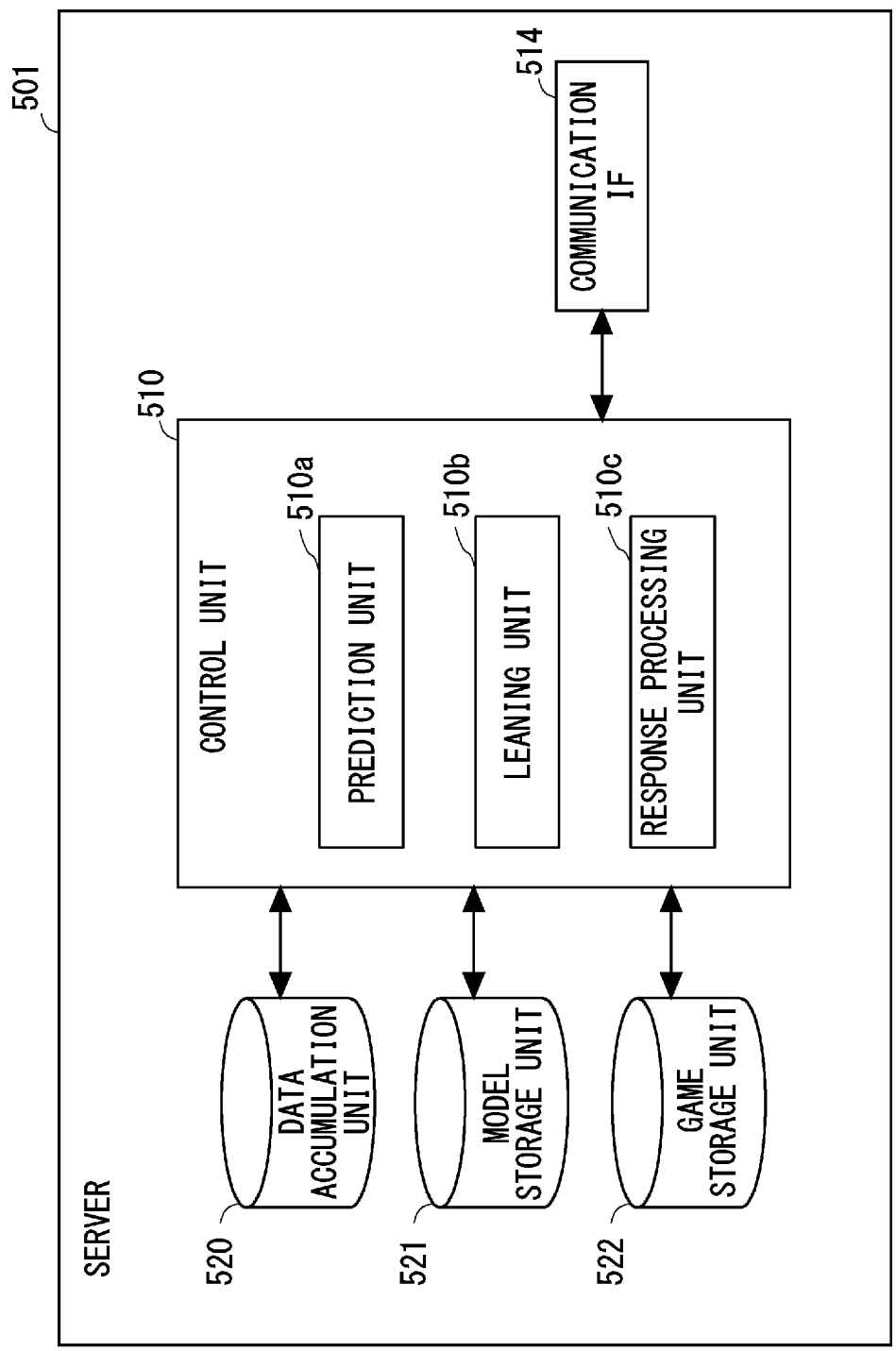
FIG. 12 is a block diagram showing an example of a configuration of a server in a rehabilitation support system according to a third embodiment.
Figure 13:
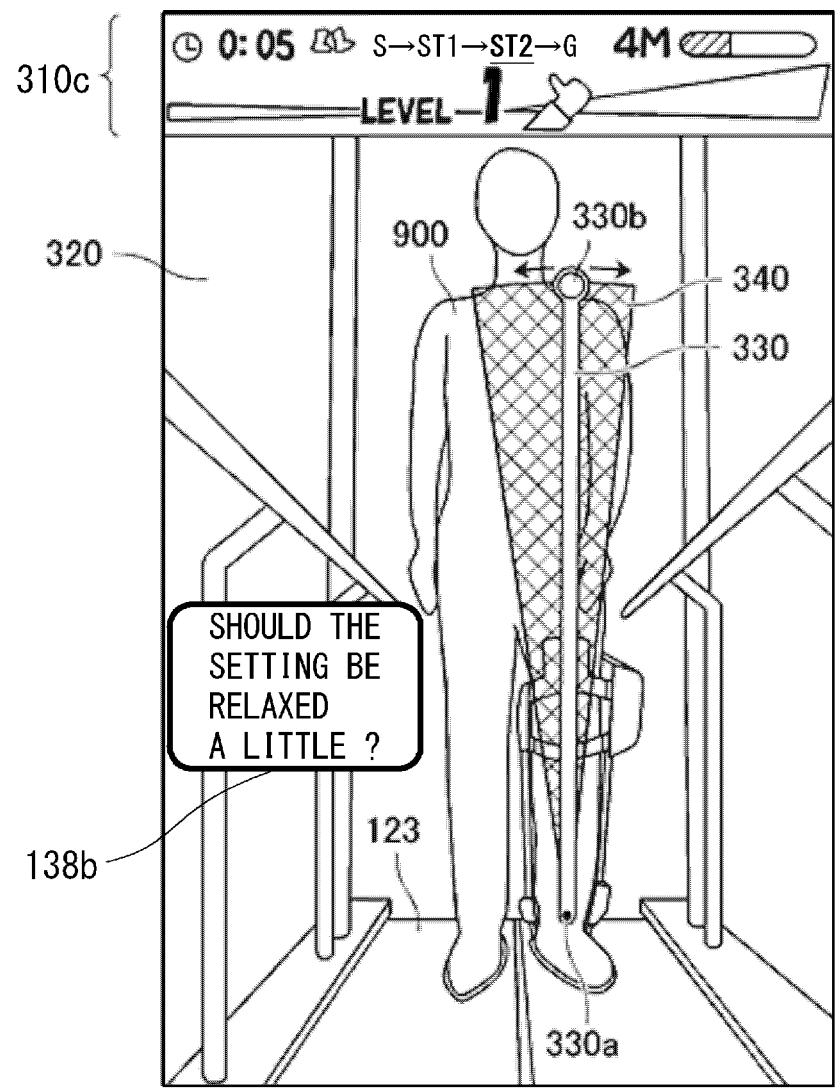
FIG. 13 shows an example of an image presented to a trainee in a rehabilitation support process according to the third embodiment.

A third embodiment will be described with reference to FIGS. 12 and 13 and the like. FIG. 12 shows an example of a configuration of a server in a rehabilitation support system according to the third embodiment, and FIG. 13 shows an example of an image presented to a trainee in a rehabilitation support process according to this embodiment. Although the detailed description of a rehabilitation support system according to this embodiment is omitted, it may include a rehabilitation support apparatus such as the walking training apparatus 100 described in the first embodiment. Further, although it is not specifically described, the various examples described above in the first and second embodiments can also be applied to this embodiment, except for the following differences. Further, effects similar to those described above can be obtained.

As shown in FIG. 12, in addition to the configuration of the server 500 shown in FIG. 4, a game(s) (a program(s) of a game(s)) capable of presenting a state of the training of the trainee 900 to the trainee 900 may be incorporated in a server 501 in an executable state. Therefore, the server 501 includes a game storage unit 522, and may load the game through the control unit 510 and execute the loaded game. The input/output of the game is performed by having the response processing unit 510c communicate with the walking training apparatus 100 through the communication IF 514. In this way, it is possible to introduce a game-playing feeling into the walking training.

Further, in this embodiment, it is possible to include, as FB control, control for changing a display form in a game. In this case, the FB unit can be included in a game on the server 501 side. For example, it is possible to include, as FB control, a change in the display form, i.e., to train the trained model so that FB information indicating a change in the display form is included in an output parameter of the trained model. Further, as the change in the display form, the prediction unit 510a passes, to the game, a command of a result output as an output parameter among various commands indicating changes in the display form, and the game is executed in accordance with this command. Alternatively, it is possible to include a notified motivational level in an output parameter and to make the game function as the FB unit. In this case, the game can change the display form in the game according to the notified motivation level.

Further, as described in the first embodiment, the FB information may include a setting parameter in the walking training apparatus 100 when the trainee 900 performs rehabilitation. Further, in this embodiment, this setting parameter may include a setting for selecting a type of the game that is played during the walking training. In this way, it is possible to construct a learning model so that it can predict, as the FB control, control for selecting a type of the game.

For example, in a GUI image 138c shown in FIG. 13, a status area 310c is displayed in place of the status area 310 in the GUI image 138a shown in FIG. 11. Note that the score indicator indicates names of stations (e.g., train stations) (in this example, Start S, ST1, ST2 and Goal G). Further, it is indicated that the trainee is currently in the ST2. This feature provides a game-playing feeling to the walking training and is an example of a travelling game in which the user (i.e., the trainee) proceeds through stations (e.g., train stations). Further, in addition, it is possible to display (i.e., superimpose) a pop-up image 138d showing a conversation with the trainee 900 on the GUI image 138c. By changing the display form according to the notified motivation level, it is possible to enhance the motivation by, for example, adopting coloring according to the notified motivation level.

Further, in this embodiment, it is possible to include, as the FB control, control for changing the game. Therefore, in the server 501, a plurality of games are incorporated in the game storage unit 522 so that they can be executed by the control unit 510. For example, although not shown in the drawings, it is possible to use, as the score indicator in the status area 310c shown in FIG. 13, one in which names of various world heritages are shown so that as if the trainee goes around through these world heritages. For example, as described that the type of the game is included in the setting parameter in the first embodiment, it is possible to train the trained model so that FB information indicating a change of a game is included in the output parameter of the trained model. Further, regarding the change of the game (the change of the type), the prediction unit 510a passes, to the response processing unit 510c, a command of a result output as an output parameter among various commands indicating changes of the game, and the response processing unit 510c can perform the game in accordance with this command. Alternatively, it is possible to include a notified motivational level in an output parameter and to make the response processing unit 510c function as the FB unit. In this case, the response processing unit 510c can change the display form in the game according to the notified motivation level. For example, it is possible to adopt a type of the game according to the motivation level by changing the game according to the motivation information, and thereby to enhance the motivation.

Further, as described above, the second embodiment can also be applied in this embodiment. That is, in the rehabilitation support system according to this embodiment, all the functions described above may be provided on the walking training apparatus 100 side, such as including a game storage unit that stores games so that they can be executed by the overall control unit 210 on the walking training apparatus 100 side as in the case of the game storage unit 522. In this way, it is possible to construct the rehabilitation support system according to this embodiment by using the walking training apparatus 100 alone.

Alternative Example

Each of the above-described embodiments is described by using an example in which the trainee 900 is a hemiplegic patient who has a disorder in one of his/her legs. However, the walking training apparatus 100 can also be applied to a patient whose legs are both paralyzed. In this case, the patient does training with walking assistance apparatuses 120 attached to both legs. In this case, abnormal walking may be evaluated for each of the diseased legs. The degree of recovery can be individually determined for each diseased leg by independently evaluating abnormal walking for each leg.

Further, although it is not shown in the drawings, the walking training apparatus may be an apparatus that is not equipped with the treadmill 131 of the walking training apparatus 100 shown in FIG. 1, so that the trainee 900 can actually move in the space surrounded by the frame 130. In this case, the frame 130 may be formed so that it has a large length in the traveling direction. Further, it may adopt a configuration in which the harness pulling unit 112, the front pulling unit 135, and the rear pulling unit 137 are moved along guide rails by a motor(s) (not shown) as the trainee 900 moves. Since the trainee 900 actually moves relative to the floor surface, he/she can feel a sense of accomplishment of rehabilitation training more effectively. Needless to say, the walking training apparatus is not limited to these configuration examples.

Further, each of the above-described embodiments is described on the assumption that the training staff member 901 is a human being. However, as a substitute, a non-human training assistant (e.g., a mechanical or artificial training assistant) may be employed. As the artificial training assistant, there are various types of assistants such as a humanoid robot, a voice assistant program, and a display assistant program. As an example in which a voice assistant program assists the trainee by voice, it is possible to give encouraging talks such as "Please lean your upper body further to the right", "Please hold the handrails", and "Please slow down your walking speed".

When the training assistant is a computer program, it can be incorporated in the walking training apparatus 100 in an executable manner. Alternatively, the program may also be incorporated, in an executable manner, in a portable terminal such as a mobile phone (including a smartphone), a mobile PC, or an external server capable of communicating with the walking training apparatus 100. Further, the artificial training assistant may also include a program with artificial intelligence (an AI program).

Further, a plurality of artificial training assistants may be made available when walking training is performed in the walking training apparatus 100, and each of them may be separately managed in a distinguishable manner. That is, even when the training assistant is an artificial training assistant, the training assistant can be distinguished from other training assistants as in the case of the human training staff member.

Further, when an artificial training assistant is used, examples of the data (the assistant data) related to the artificial training assistant corresponding to the data related to the training staff member 901 in the above-described item (4) include the below-shown data. The examples include functions (such as a voice assist function and an assistance function using a video display) of the artificial training assistant (the program), and a name and a version of the program. Further, when the program is a type of an AI program that learns during its operation, the examples include a learning algorithm, a degree of learning, a learning time, and the number of times of learning.

Further, in the case where a plurality of training assistants (irrespective of whether the assistant is a human assistant or a non-human assistant) simultaneously assist the rehabilitation, the rehabilitation data may include assistant data of the plurality of assistants as in the case of the plurality of human training staff members as described above. Further, each assistant data may also include information indicating whether the assistant is a main training assistant or an assistance training assistant. In addition to or instead of the aforementioned information, each assistant data may include information indicating what kind of assistance is provided.

A notification will be described. For example, when a notification to an artificial training assistant, rather than the human assistant such as the training staff member 901, is required, the notification control unit 210d may notify the artificial training assistant. The notification may be directly provided through communication. Alternatively, the notification may be provided by a video image or a voice as in the case of the human assistant and the video or voice notification may be detected by the artificial training assistant. Further, the artificial training assistant may be configured so as to be able to change the setting or the like of the walking training apparatus 100 through communication or a direct-touch operation. In this way, even the artificial training assistant can give rehabilitation support while taking the motivation of the trainee into consideration.

Further, a rehabilitation support apparatus described in each embodiment may be formed as a rehabilitation support system by using a plurality of apparatuses. Similarly, the walking training apparatus may be formed as a walking training system by using a plurality of apparatuses, and the training support apparatus may be formed as a training support system by using a plurality of apparatuses. Further, for example, a server (a server apparatus) described in each embodiment may not be equipped with the learning apparatus but may be equipped only with the trained model. Further, the server may be equipped with all of or only some of the functions of the learning apparatus. Further, a server apparatus described in each embodiment may include at least some of the functions and parts described as the functions and parts of the rehabilitation support apparatus.

Further, as described above, a rehabilitation support apparatus according to each embodiment may be an apparatus for supporting other kinds of rehabilitation, i.e., rehabilitation other than the walking training, or for supporting training other than the rehabilitation. In such a case, the learning apparatus according to each embodiment may be a learning apparatus that generates a trained model that is adapted to that apparatus. For example, it is possible to use input parameters and output parameters corresponding to the type of the rehabilitation or the type of the training. Examples of the training other than the rehabilitation include exercises such as walking and running and training. Further, a training support apparatus corresponding to the type of the training can be used. Further, the index data in the case of the training other than the rehabilitation may be data indicating the degree of an improvement in a physical function of the trainee instead of the degree of recovery of the trainee. The degree of an improvement in a physical function may include an improvement in a muscle strength by an exercise or the like and/or an improvement in endurance. Further, even when the training is the rehabilitation, the index data may be data indicating the degree of an improvement in a physical function of the trainee. In this case, the degree of an improvement in a physical function may include the degree of recovery by the rehabilitation or the like. Further, in the case of the training other than the rehabilitation, the rehabilitation data can be referred to as training data.

Further, the above-described rehabilitation support apparatus or the server apparatus may have a hardware configuration including, for example, a processor, a memory, and a communication interface. These apparatuses are implemented by making the processor load and execute a program stored in the memory.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A learning system comprising a learning unit configured to generate a learning model, the learning model being configured to receive input rehabilitation data about rehabilitation and predict feedback control to be performed during the rehabilitation, the rehabilitation being performed by a trainee using a rehabilitation support system, the rehabilitation support system being configured to perform the feedback control based on motivation information indicating a motivation of the trainee, wherein
the rehabilitation data includes at least training data including data acquired by sensors, provided in the rehabilitation support system, during the rehabilitation using the rehabilitation support system, the motivation information of the trainee and feedback information indicating the feedback control, and the rehabilitation data further includes setting parameters of the rehabilitation support system, and data related to the trainee, and
the learning unit generates the learning model using the rehabilitation data that is obtained when the motivation information indicates that the motivation of the trainee is improved.

2. The learning system according to claim 1, wherein the feedback information includes a setting parameter in the rehabilitation support system when the trainee performs the rehabilitation.

3. The learning system according to claim 1, wherein the feedback information includes a content of a notification that is provided in the rehabilitation support system when the trainee performs the rehabilitation.

4. The learning system according to claim 1, wherein the motivation information includes at least line-of-sight information of the trainee.

5. The learning system according to claim 1, wherein the rehabilitation data includes data indicating a preference of the trainee input to the rehabilitation support system.

6. The learning system according to claim 1, wherein the learning system further comprises an extraction unit configured to extract, from rehabilitation data of a plurality of trainees, rehabilitation data of a trainee whose state indicated by index data at an early stage of the training is at a predetermined level, wherein
the learning unit generates the learning model for the trainee having the predetermined level by using the rehabilitation data extracted by the extraction unit as an input.

7. The learning system according to claim 6, wherein the extraction unit extracts rehabilitation data of a trainee of which a combination of the index data at the early stage of the training and the index data at the time when the index data is at the predetermined level is a predetermined combination.

8. A non-transitory computer readable medium storing a trained model, the trained model being a learning model that has been generated by the learning system according to claim 1.

9. A rehabilitation support system capable of accessing a trained model, the trained model being a learning model generated by the learning system according to claim 1, the rehabilitation support system comprising:
a prediction acquisition unit configured to input the rehabilitation data of a trainee who starts or is performing training to the trained model and obtains a result of a prediction of the feedback control to be performed; and
a feedback unit configured to perform the feedback control obtained by the prediction acquisition unit.

10. The learning system according to claim 1, wherein the motivation information is comprised of one or more of camera information comprised of at least one of line of sight of the trainee, an orientation of the head of the trainee, and a facial expression of the trainee, sensor information indicating an inclination angle of the trunk of the trainee, and microphone information comprised of at least one of attitude and ratio of speech from a conversation by the trainee.

11. A learning method comprising a learning step of generating a learning model, the learning model being configured to receive input rehabilitation data about rehabilitation and predict feedback control to be performed during the rehabilitation, the rehabilitation being performed by a trainee using a rehabilitation support system, the rehabilitation support system being configured to perform the feedback control based on motivation information indicating a motivation of the trainee, wherein
the rehabilitation data includes at least training data including data acquired by sensors, provided in the rehabilitation support system, during the rehabilitation using the rehabilitation support system, the motivation information of the trainee and feedback information indicating the feedback control, and the rehabilitation data further includes setting parameters of the rehabilitation support system, and data related to the trainee, and
in the learning step, the learning model is generated using the rehabilitation data that is obtained when the motivation information indicates that the motivation of the trainee is improved.

12. A method for supporting rehabilitation performed in a rehabilitation support system, the rehabilitation support system being capable of accessing a trained model, the trained model being a learning model generated by the learning method according to claim 11, the method including:
an acquisition step of inputting the rehabilitation data of a trainee who starts or is performing training to the trained model and obtaining a result of a prediction of the feedback control to be performed; and
a feedback step of performing the feedback control obtained in the acquisition step.

13. A non-transitory computer readable medium storing a trained model, the trained model being a learning model that has been generated by the learning method according to claim 11.

14. The learning method according to claim 11, wherein the motivation information is comprised of one or more of camera information comprised of at least one of line of sight of the trainee, an orientation of the head of the trainee, and a facial expression of the trainee, sensor information indicating an inclination angle of the trunk of the trainee, and microphone information comprised of at least one of attitude and ratio of speech from a conversation by the trainee.

15. A non-transitory computer readable medium storing a program for causing a computer to perform a learning step of generating a learning model, the learning model being configured to receive input rehabilitation data about rehabilitation and predict feedback control to be performed, the rehabilitation being performed by a trainee using a rehabilitation support system, the rehabilitation support system being configured to perform the feedback control based on motivation information indicating a motivation of the trainee, wherein
the rehabilitation data includes at least training data including data acquired by sensors, provided in the rehabilitation support system, during the rehabilitation using the rehabilitation support system, the motivation information of the trainee and feedback information indicating the feedback control, and the rehabilitation data further includes setting parameters of the rehabilitation support system, and data related to the trainee, and
in the learning step, the learning model is generated using the rehabilitation data that is obtained when the motivation information indicates that the motivation of the trainee is improved.

16. A non-transitory computer readable medium storing a rehabilitation support program for a computer of a rehabilitation support system, the rehabilitation support system being capable of accessing a trained model, the trained model being a learning model trained by the program stored in the non-transitory computer readable medium according to claim 15, the rehabilitation support program being configured to cause the computer to perform:
an acquisition step of inputting the rehabilitation data of a trainee who starts or is performing training to the trained model and obtaining a result of a prediction of the feedback control to be performed; and
a feedback step of performing the feedback control obtained in the acquisition step.

17. A non-transitory computer readable medium storing a trained model, the trained model being a learning model that has been generated by the program stored in the non-transitory computer readable medium according to claim 15.

* * * * *